(12) United States Patent
Dean et al.

(10) Patent No.: US 6,300,320 B1
(45) Date of Patent: Oct. 9, 2001

(54) MODULATION OF C-JUN USING INHIBITORS OF PROTEIN KINASE C

(75) Inventors: Nicholas M. Dean, Olivenhain; Robert McKay, La Mesa, both of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/225,749

(22) Filed: Jan. 5, 1999

(51) Int. Cl.$^7$ .......................... A61K 31/70; A01N 43/04; C07H 21/04; C12N 15/85; C12N 15/86

(52) U.S. Cl. .......................... 514/44; 536/24.5; 435/325; 435/375

(58) Field of Search .................... 536/24.5, 23.1, 536/24.3; 435/6, 91.1, 375, 371

(56) References Cited

U.S. PATENT DOCUMENTS

| | | |
|---|---|---|
| 3,687,808 | 8/1972 | Merigan et al. . |
| 4,309,404 | 1/1982 | DeNeale et al. . |
| 4,309,406 | 1/1982 | Guley et al. . |
| 4,469,863 | 9/1984 | Ts'o et al. . |
| 4,476,301 | 10/1984 | Imbach et al. . |
| 4,556,552 | 12/1985 | Porter et al. . |
| 4,587,044 | 5/1986 | Miller et al. . |
| 4,605,735 | 8/1986 | Miyoshi et al. . |
| 4,667,025 | 5/1987 | Miyoshi et al. . |
| 4,704,295 | 11/1987 | Porter et al. . |
| 4,762,779 | 8/1988 | Snitman . |
| 4,789,737 | 12/1988 | Miyoshi et al. . |
| 4,824,941 | 4/1989 | Gordon et al. . |
| 4,828,979 | 5/1989 | Klevan et al. . |
| 4,835,263 | 5/1989 | Nguyen et al. . |
| 4,845,205 | 7/1989 | Huynh Dinh et al. . |
| 4,876,335 | 10/1989 | Yamane et al. . |
| 4,904,582 | 2/1990 | Tullis . |
| 4,948,882 | 8/1990 | Ruth . |
| 4,958,013 | 9/1990 | Letsinger . |
| 4,981,957 | 1/1991 | Lebleu et al. . |
| 5,023,243 | 6/1991 | Tullis . |
| 5,034,506 | 7/1991 | Summerton et al. . |
| 5,082,830 | 1/1992 | Brakel et al. . |
| 5,109,124 | 4/1992 | Ramachandran et al. . |
| 5,112,963 | 5/1992 | Pieles et al. . |
| 5,118,800 | 6/1992 | Smith et al. . |
| 5,118,802 | 6/1992 | Smith et al. . |
| 5,130,302 | 7/1992 | Spielvogel et al. . |
| 5,134,066 | 7/1992 | Rogers et al. . |
| 5,138,045 | 8/1992 | Cook et al. . |
| 5,166,315 | 11/1992 | Summerton et al. . |
| 5,175,273 | 12/1992 | Bischofberger et al. . |
| 5,177,196 | 1/1993 | Meyer, Jr. et al. . |

(List continued on next page.)

FOREIGN PATENT DOCUMENTS

| | | |
|---|---|---|
| WO 92/20823 | 11/1992 | (WO) . |
| WO 93/24510 | 12/1993 | (WO) . |
| WO 9729780 | * 8/1997 | (WO) . |

OTHER PUBLICATIONS

Wang et al. Antisense expression of protein kinase C–alpha inhibits the growth of human hepatoma BEL–7402 cell. Progress in Natural Science, vol. 7, No. 2, pp. 194–201, Apr. 1997.*

Andrea D. Branch, A good antisense molecule is hard to find, TIBS, 47–48, Feb. 1998.*

Trisha Gura, Antisense Has Growing Pains, Science, pp. 575–577, Oct. 1995.*

Stanley Crooke, Antisense '97: A roundtable on the state of the industry, Nature Biotechnology, p. 522, Jun. 1997.*

Stanley Crooke, Antisense Research and Applications, Chapter 1, Basic Principles of Antisense Therapeutics, Springer–Verlag Press, Berlin, Heidelberg, New York, p. 3, Jul. 1998.*

Desai et al., Characterization of Retinoic Acid–induced AP–1 Activity in B16 Mouse Melanoma Cells. JBC, vol. 272, No. 19, pp. 12809–12815, May, 9, 1997.*

Ahmad, S. et al., "Antisense Expression of Protein Kinase Cα Inhibits the Growth and Tumorigenicity of Human Glioblastoma Cells", *Neurosurgery*, 1994, 35, 904–909.

Anderson, A.J. et al., "DNA Damage and Apoptosis in Alzheimer's Disease: Colocalization with c–Jun Immunoreactivity, Relationship to Brain Area, and Effect of Postmortem Delay", *J. Neurosci.*, 1996, 16(5), 1710–1719.

Ballester et al., "Fate of Immunoprecipitable Protein Kinase C in $GH_3$ Cells Treated with Phorbol 12–Myristate 13–Acetate", *J. Biol. Chem.*, 1985, 260(28), 15194–15199.

Benussi, L. et al., "Specific role for protein kinase Cα in the constitutive and regulated secretion of amyloid precursor protein in human skin fibroblasts", *Neurosci. Lett.*, 1998, 240, 97–101.

Berge, S.M. et al., "Pharmaceutical Salts", *J. Pharm. Sci.*, 1977, 66, 1–19.

Berkow et al. (eds.), "Oncology", *The Merck Manual of Diagnosis and Therapy*, 15th Edition, Rahway, N.J., 1987, 1206–1228.

Bohmann, D. et al., "Human Proto–Oncogene c–jun Encodes a DNA Binding Protein with Structural and Functional Properties of Transcription Factor AP–1", *Science*, 1987, 238, 1386–1392.

Boyle, W.J. et al., "Activation of Protein Kinase C Decreases Phosphorylation of c–Jun at Sites That Negatively Regulate Its DNA–Binding Activity", *Cell*, 1991, 8, 573–584.

(List continued on next page.)

*Primary Examiner*—John L. LeGuyader
*Assistant Examiner*—Janet Epps
(74) *Attorney, Agent, or Firm*—Woodcock Washburn Kurtz Mackiewicz & Norris LLP

(57) ABSTRACT

Methods and compositions are provided for modulating c-jun expression using inhibitors of PKC-α. In preferred embodiments, the specific inhibitors are antisense oligonucleotides hybridizable to PKC-α. In preferred embodiments, the oligonucleotides contain one or more chemical modifications. Methods of modulating c-jun expression and of treating animals suffering from disease amenable to therapeutic intervention by modulating c-jun expression are disclosed

4 Claims, 11 Drawing Sheets

U.S. PATENT DOCUMENTS

| | | |
|---|---|---|
| 5,185,444 | 2/1993 | Summerton et al. . |
| 5,188,897 | 2/1993 | Suhadolnik et al. . |
| 5,214,134 | 5/1993 | Weis et al. . |
| 5,214,136 | 5/1993 | Lin et al. . |
| 5,216,141 | 6/1993 | Benner . |
| 5,218,105 | 6/1993 | Cook et al. . |
| 5,235,033 | 8/1993 | Summerton et al. . |
| 5,245,022 | 9/1993 | Weis et al. . |
| 5,254,469 | 10/1993 | Warren, III et al. . |
| 5,258,506 | 11/1993 | Urdea . |
| 5,262,536 | 11/1993 | Hobbs, Jr. . |
| 5,264,423 | 11/1993 | Cohen et al. . |
| 5,264,562 | 11/1993 | Matteucci . |
| 5,264,564 | 11/1993 | Matteucci . |
| 5,272,250 | 12/1993 | Spielvogel et al. . |
| 5,276,019 | 1/1994 | Cohen et al. . |
| 5,278,302 | 1/1994 | Caruthers et al. . |
| 5,286,717 | 2/1994 | Cohen et al. . |
| 5,292,873 | 3/1994 | Rokita et al. . |
| 5,317,098 | 5/1994 | Shizuya et al. . |
| 5,319,080 | 6/1994 | Leumann . |
| 5,321,131 | 6/1994 | Agrawal et al. . |
| 5,359,044 | 10/1994 | Cook et al. . |
| 5,367,066 | 11/1994 | Urdea et al. . |
| 5,371,241 | 12/1994 | Brush et al. . |
| 5,391,723 | 2/1995 | Priest . |
| 5,393,878 | 2/1995 | Leumann . |
| 5,399,676 | 3/1995 | Froehler . |
| 5,405,938 | 4/1995 | Summerton et al. . |
| 5,405,939 | 4/1995 | Suhadolnik et al. . |
| 5,414,077 | 5/1995 | Lin et al. . |
| 5,416,203 | 5/1995 | Letsinger . |
| 5,432,272 | 7/1995 | Benner . |
| 5,434,257 | 7/1995 | Matteucci et al. . |
| 5,446,137 | 8/1995 | Maag et al. . |
| 5,451,463 | 9/1995 | Nelson et al. . |
| 5,453,496 | 9/1995 | Caruthers et al. . |
| 5,455,233 | 10/1995 | Spielvogel et al. . |
| 5,457,187 | 10/1995 | Gmeiner et al. . |
| 5,459,255 | 10/1995 | Cook et al. . |
| 5,466,677 | 11/1995 | Baxter et al. . |
| 5,466,786 | 11/1995 | Buhr et al. . |
| 5,470,967 | 11/1995 | Huie et al. . |
| 5,476,925 | 12/1995 | Letsinger et al. . |
| 5,484,908 | 1/1996 | Froehler et al. . |
| 5,486,603 | 1/1996 | Buhr . |
| 5,489,677 | 2/1996 | Sanghvi et al. . |
| 5,502,177 | 3/1996 | Matteucci et al. . |
| 5,510,475 | 4/1996 | Agrawal et al. . |
| 5,512,439 | 4/1996 | Hornes et al. . |
| 5,512,667 | 4/1996 | Reed et al. . |
| 5,514,785 | 5/1996 | Van Ness et al. . |
| 5,519,126 | 5/1996 | Hecht . |
| 5,519,134 | 5/1996 | Acevedo et al. . |
| 5,525,465 | 6/1996 | Haralambidis et al. . |
| 5,525,711 | 6/1996 | Hawkins et al. . |
| 5,536,821 | 7/1996 | Agrawal et al. . |
| 5,539,082 | 7/1996 | Nielsen et al. . |
| 5,541,306 | 7/1996 | Agrawal et al. . |
| 5,541,307 | 7/1996 | Cook et al. . |
| 5,541,313 | 7/1996 | Ruth . |
| 5,545,730 | 8/1996 | Urdea et al. . |
| 5,550,111 | 8/1996 | Suhadolnik et al. . |
| 5,552,538 | 9/1996 | Urdea et al. . |
| 5,552,540 | 9/1996 | Haralambidis . |
| 5,561,225 | 10/1996 | Maddry et al. . |
| 5,563,253 | 10/1996 | Agrawal et al. . |
| 5,565,552 | 10/1996 | Magda et al. . |
| 5,567,810 | 10/1996 | Weis et al. . |
| 5,567,811 | 10/1996 | Misiura et al. . |
| 5,571,799 | 11/1996 | Tkachuk et al. . |
| 5,574,142 | 11/1996 | Meyer, Jr. et al. . |
| 5,576,427 | 11/1996 | Cook et al. . |
| 5,578,717 | 11/1996 | Urdea et al. . |
| 5,578,718 | 11/1996 | Cook et al. . |
| 5,580,731 | 12/1996 | Chang et al. . |
| 5,585,481 | 12/1996 | Arnold, Jr. et al. . |
| 5,587,361 | 12/1996 | Cook et al. . |
| 5,587,371 | 12/1996 | Sessler et al. . |
| 5,587,469 | 12/1996 | Cook et al. . |
| 5,591,584 | 1/1997 | Chang et al. . |
| 5,591,722 | 1/1997 | Montgomery et al. . |
| 5,594,121 | 1/1997 | Froehler et al. . |
| 5,595,726 | 1/1997 | Magda et al. . |
| 5,596,086 | 1/1997 | Matteucci et al. . |
| 5,596,091 | 1/1997 | Switzer . |
| 5,597,696 | 1/1997 | Linn et al. . |
| 5,597,909 | 1/1997 | Urdea et al. . |
| 5,599,923 | 2/1997 | Sessler et al. . |
| 5,599,928 | 2/1997 | Hemmi et al. . |
| 5,602,240 | 2/1997 | De Mesmaeker et al. . |
| 5,608,046 | 3/1997 | Cook et al. . |
| 5,610,289 | 3/1997 | Cook et al. . |
| 5,610,300 | 3/1997 | Altmann et al. . |
| 5,614,617 | 3/1997 | Cook et al. . |
| 5,618,704 | 4/1997 | Sanghvi et al. . |
| 5,623,070 | 4/1997 | Cook et al. . |
| 5,625,050 | 4/1997 | Beaton et al. . |
| 5,627,053 | 5/1997 | Usman et al. . |
| 5,633,360 | 5/1997 | Bischofberger et al. . |
| 5,639,873 | 6/1997 | Barascut et al. . |
| 5,646,265 | 7/1997 | McGee . |
| 5,658,873 | 8/1997 | Bertsch-Frank et al. . |
| 5,663,312 | 9/1997 | Chaturvedula . |
| 5,670,633 | 9/1997 | Cook et al. . |
| 5,677,437 | 10/1997 | Teng et al. . |
| 5,677,439 | 10/1997 | Weis et al. . |
| 5,681,941 | 10/1997 | Cook et al. . |
| 5,688,941 | 11/1997 | Cook et al. . |
| 5,700,920 | 12/1997 | Altmann et al. . |
| 5,714,331 | 2/1998 | Buchardt et al. . |
| 5,719,262 | 2/1998 | Buchardt et al. . |

OTHER PUBLICATIONS

Brunton, L.L., "Agents Affecting Gastrointestinal Water Flux and motility; Emesis and Antiemetics; Bile Acids and Pancreatic Enzymes", *Goodman & Gilman's The Pharmacological Basis of Therapeutics*, 9th Ed., Hardman et al. (Eds.), McGraw–Hill, New York, 1996, Chapter 38, 934–935.

Buur, A. et al., "Penetration of 5–Fluorouracil and prodrugs across the intestine of the albino rabbit: Evidence for shift in absorption site from the upper to the lower region of the gastrointestinal tract by prodrugs", *J. Controlled Release*, 1990, 14, 43–51.

Chen, CC. et al., "Role of Protein Kinase C Subtypes α and δ in the Regulation of Bradykinin–Stimulated Phosphoinositide Breakdown in Astrocytes", *Mol. Pharmacol.*, 1995, 39, 39–47.

Chiang, M.Y. et al., "Antisense Oligonucleotides Inhibit Intercellular Adhesion Molecule 1 Expression by Two Distinct Mechanisms", *J. Biol. Chem.*, 1991, 266, 18162–18171.

Chonn, A. et al., "Recent advances in liposomal drug–delivery systems", *Curr. Opin. Biotechnology*, 1995, 6, 698–708.

Crooke, S.T. et al., "Pharmacokinetic Properties of Several Novel Oligonucleotide Analogs in mice", *J. Pharmacol. Exp. Therapeutics*, 1996, 277, 923–937.

De Mesmaeker, A. et al., "Antisense Oligonucleotides", *Acc. Chem. Res.*, 1995, 28, 366–374.

Dooley, S. et al., "Constitutive expression of c–fos and c–jun, overexpression of ets–2, and reduced expression of metastasis suppressor geen nm23–H1 in rheumatoid arthritis", *Ann. Rheum. Dis.*, 1996, 55, 298–304.

El–Hariri, L.M. et al., "The Mitigating Effects of Phosphatidylcholines on Bile Salt–and Lysophosphatidylcholine–induced Membrane Damage", *J. Pharm. Pharmacol.*, 1992, 44, 651–654.

Englisch, U. et al., "Chemically Modified Oligonucleotides as Probes and Inhibitors", *Angew. Chem. Int. Ed. Eng.*, 1991, 30, 613–629.

Ferrer, I. et al., "Strong c–Jun immunoreactivity is associated with apoptotic cell death in human tumors of the central nervous system", *Neurosci. Lett.*, 1996, 214, 49–52.

Finkenzeller, G. et al., "Sequence of Human Protein Kinase C," *Nucleic Acids Research*, 1990, 18, 2183.

Franchi, A. et al., "Immunohistochemical detection of c–fos and c–jun expression in osseous and cartilaginous tumours of the skeleton", *Virchows Arch.*, 1998, 432, 515–519.

Fung, H. et al., "Inhibition of Protein Kinase C Prevents Asbestos–induced c–fos and c–jun Proto–Oncogene Expression in Mesothelial Cells", *Cancer Res.*, 1997, 57, 3101–3105.

Gescher et al., "Protein kinase C–a novel target for rational anti–cancer drug design?", *Anti–Cancer Drug Design*, 1989, 4, 93–105.

Godson, C. et al., "Inhibition of Expression of Protein Kinase C α by Antisense cDNA Inhibits Phorbol Ester–meidated Arachidonate Release", *J. Biol. Chem.*, 1993, 268, 11946–11950.

Hegemann, L. et al., "Biochemical Pharmacology of Protein Kinase C and its Relevance for Dermatology", *Pharmacology of the Skin*, Mukhtar, H. (ed), CRC Press, Boca Raton, 1992, Ch.22, 357–368.

Hidaka et al., "Pharmacology of the isoquinoline sulfonamide protein kinase C inhibitors", *Trends in Pharm. Sci.*, 1987, 8, 162–164.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kawasaki, A.M. et al., "Uniformly Modified 2'–Deoxy–2'–fluoro Phosphorothioate Oligonucleotides as Nuclease–Resistant Antisense Compounds with High Affinity and Specificity for RNA Targets", *J. Med. Chem.*, 1993, 831–841.

Kroschwitz, J.I., "Polynucleotides", *Concise Encyclopedia of Polymer Science and Engineering*, 1990, John Wiley & Sons, New York, 858–859.

Krug et al., "Evidence for Increased Synthesis as Well as Increased Degradation of Protein Kinase C after Treatment of Human Osteosarcoma Cells with Phorbol Ester", *J. Biol. Chem.*, 1987, 262(24), 11852–11856.

LaPorta, C.A. et al., "Inhibition of protein kinase C–α isoform enhances the P–glycoprotein expression and the survival of LoVo human colon adenocarcinoma cells to doxorubicin exposure", *Br. J. Cancer*, 1998, 78(10), 1283–1287.

Lee, V.H.L. et al., "Mucosal Penetration Enhancers For Facilitation of Peptide and Protein Drug Absorption", *Crit. Rev. Ther. Drug Carrier Systems*, 1991, 8, 91–192.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Liao et al., "Effect of α–Protein Kinase C Neutralizing Antibodies and the Pseudosubstrate Peptide on Phosphorylation, Migration, and Growth of REF52 Cells", *Cell Growth Differ.*, 1993, 4, 309–316.

Manoharan M. et al., "Cholic Acid–Oligonucliotide Conjugates for Antisense Applications", *Bioorganic Med. Chem. Letts.*, 1994, 4, 1053–1060.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Oligonucleotide Conjugates: Alteration of the Pharmacokinetic Properties of Antisense Agents", *Nucleosides and Nucleotides*, 1995, 14, 969–973.

Manoharan, M. et al., "Lipidic Nucleic Acids", *Tetrahedron Letts.*, 1995, 36, 3651–3654.

Manoharan, M. et al., "Chemical Modifications to Improve Uptake and Bioavailability of Antisense Oligonucleotides", *Annals NY Acad. Sciences*, 1992, 660, 306–309.

Martin, P., "Ein neuer Zugang zu 2'–O–Alkylribonucleosiden und Eigenschaften deren Oligonucleotide", *Helvetica Chemica Acta*, 1995, 78, 486–504.

Mishra, R.K. et al., "Improved leishmanicidal effect of phosphorotioate antisense oligonucleotides by LDL–medicated delivery", *Biochim. Et Biophysica*, 1995, 1264, 229–237.

Muranishi, S., "Absorption Enhancers", *Crit. Rev. Ther. Drug Carrier Systems*, 1990, 7, 1–33.

Nielsen, P.E. et al., "Sequence–Selective Recognition of DNA by Strand Displacement with a Thymine–Substituted Polyamide", *Science*, 1991, 254, 1497–1500.

Nishizuka, "The molecular heterogeniety of protein kinase C and its implications for cellular regulation", *Nature*, 1988, 334, 661–665.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Osada et al., "A Phorbol Ester Receptor/Protein Kinase, nPKCη, a New Member of the Protein Kinase C Family Predominantly Expressed in Lung and Skin", *J. Biol. Chem.*, 1990, 265(36), 22434–22440.

Parissenti, A.M. et al., "Inhibitory Properties of the Regulartory Domains of Human Protein Kinase Cα and Mouse Protein Kinase Cε", *J. Biol. Chem.*, 1998, 273(15), 8940–8945.

Parker et al., "The Complete Primary Structure of Protein Kinase C—The Major Phorbol Ester Receptor", *Science*, 1986, 233, 853–866.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Sanghvi, Y.S. et al., "Antisense oligodeoxynucleotides: synthesis, biophysical and biological evaluation of oligodeoxynucleotides containing modified pyrimidines", *Nucl. Acids Res.*, 1993, 21, 3197–3203.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Seachrist, L. (ed.), "FDA Approves Isis' Vitravene For AIDS–Related Eye Virus", *BioWorld Today*, Aug. 28, 1998, vol. 9(166), 1 page.

Shea, R.G. et al., "Synthesis, hybridization properties and antiviral activity of lipid–oligodeoxynucletide conjugates", *Nucl. Acids Res.*, 1990, 18, 3777–3783.

Skopelitou, A. et al., "p53 and c–jun Expression in Urinary Bladder Transitional Cell Carcinoma: Correlation with Proliferating Cell Nuclear Antigen (PCNA) Histological Grade and Clinical Stage", *Eur. Urol.*, 1997, 31, 464–471.

Spinner, D.M. et al., "c–jun Expression and Growth Stimulation in Human Ovarian Carcinoma Cell Lines Following Exposure to Cytokines", *Int. J. Cancer*, 1995, 63, 423–427.

Svinarchuk, F.P. et al., "Inhibition of HIV proliferation in MT–4 cells by antisense oligonucleotide conjugated to lipophilic groups", *Biochimie*, 1993, 79, 49–54.

Takahashi, H. et al., "The Use of a Perfluorochemical Emulsion as a Bascular Perfusate in Drug Absorption", *J. Pharm. Pharmacol.*, 1988, 40, 252–257.

Volm, M. et al., "Analysis of c–fos, c–jun, c–erbB1, c–erbB2 and c–myc in primary lung carcinomas and their lymph node metastases", *Clin. Exp. Metastasis*, 1994, 12, 329–334.

Yamashita, S. et al., "Effects of diclofenac sodium and disodium ethylenediaminetetraacetate on electrical parameters of the mucosal membrane and their relation to the permeability enhancing effects in the rat jejunum", *J. Pharm. Pharmacol.*, 1987, 39, 621–626.

Young et al., "Down–regulation of protein kinase C is due to an increased rate of degradation", *Biochem. J.*, 1987, 244, 775–779.

\* cited by examiner

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: antisense sequence

<400> SEQUENCE: 1
ccccaaccac ctcttgctcc                                                     20

<210> SEQ ID NO 2
<211> LENGTH: 20
<212> TYPE: DNA
<213> ORGANISM: Artificial Sequence
<220> FEATURE:
<223> OTHER INFORMATION: antisense sequence

<400> SEQUENCE: 2
gttctcgctg gtgagtttca                                                     20

<210> SEQ ID NO 3
<211> LENGTH: 20
<212> TYPE: DNA
<213> ORGANISM: Artificial Sequence
<220> FEATURE:
<223> OTHER INFORMATION: antisense sequence

<400> SEQUENCE: 3
aaaacgtcag ccatggtccc                                                     20

<210> SEQ ID NO 4
<211> LENGTH: 20
<212> TYPE: DNA
<213> ORGANISM: Artificial Sequence
<220> FEATURE:
<223> OTHER INFORMATION: antisense sequence

<400> SEQUENCE: 4
ggattcactt ccactgcggg                                                     20

<210> SEQ ID NO 5
<211> LENGTH: 20
<212> TYPE: DNA
<213> ORGANISM: Artificial Sequence
<220> FEATURE:
<223> OTHER INFORMATION: antisense sequence

<400> SEQUENCE: 5
gagaccctga acagttgatc                                                     20

<210> SEQ ID NO 6
<211> LENGTH: 20
<212> TYPE: DNA
<213> ORGANISM: Artificial Sequence
<220> FEATURE:
<223> OTHER INFORMATION: antisense sequence

<400> SEQUENCE: 6
cccgggaaaa cgtcagccat                                                     20

<210> SEQ ID NO 7
<211> LENGTH: 20

```
<212> TYPE: DNA
<213> ORGANISM: Artificial Sequence
<220> FEATURE:
<223> OTHER INFORMATION: antisense sequence

<400> SEQUENCE: 7
ctgcctcagc gcccctttgc                                          20

<210> SEQ ID NO 8
<211> LENGTH: 20
<212> TYPE: DNA
<213> ORGANISM: Artificial Sequence
<220> FEATURE:
<223> OTHER INFORMATION: antisense sequence

<400> SEQUENCE: 8
agtcggtgca gtggctggag                                          20

<210> SEQ ID NO 9
<211> LENGTH: 20
<212> TYPE: DNA
<213> ORGANISM: Artificial Sequence
<220> FEATURE:
<223> OTHER INFORMATION: antisense sequence

<400> SEQUENCE: 9
gcagaggctg gggacattga                                          20

<210> SEQ ID NO 10
<211> LENGTH: 20
<212> TYPE: DNA
<213> ORGANISM: Artificial Sequence
<220> FEATURE:
<223> OTHER INFORMATION: antisense sequence

<400> SEQUENCE: 10
gggctgggga ggtgtttgtt                                          20

<210> SEQ ID NO 11
<211> LENGTH: 20
<212> TYPE: DNA
<213> ORGANISM: Artificial Sequence
<220> FEATURE:
<223> OTHER INFORMATION: antisense sequence

<400> SEQUENCE: 11
cactgcgggg agggctgggg                                          20

<210> SEQ ID NO 12
<211> LENGTH: 20
<212> TYPE: DNA
<213> ORGANISM: Artificial Sequence
<220> FEATURE:
<223> OTHER INFORMATION: antisense sequence

<400> SEQUENCE: 12
agccgtggcc ttaaaatttt                                          20

<210> SEQ ID NO 13
<211> LENGTH: 20
<212> TYPE: DNA
<213> ORGANISM: Artificial Sequence
<220> FEATURE:
<223> OTHER INFORMATION: antisense sequence

<400> SEQUENCE: 13
```

-continued

```
attttcaggc ctccatatgg                                              20

<210> SEQ ID NO 14
<211> LENGTH: 20
<212> TYPE: DNA
<213> ORGANISM: Artificial Sequence
<220> FEATURE:
<223> OTHER INFORMATION: antisense sequence

<400> SEQUENCE: 14
aagagagaga ccctgaacag                                              20

<210> SEQ ID NO 15
<211> LENGTH: 20
<212> TYPE: DNA
<213> ORGANISM: Artificial Sequence
<220> FEATURE:
<223> OTHER INFORMATION: antisense sequence

<400> SEQUENCE: 15
gataatgttc ttggttgtaa                                              20

<210> SEQ ID NO 16
<211> LENGTH: 20
<212> TYPE: DNA
<213> ORGANISM: Artificial Sequence
<220> FEATURE:
<223> OTHER INFORMATION: antisense sequence

<400> SEQUENCE: 16
atggggtgca caaactgggg                                              20

<210> SEQ ID NO 17
<211> LENGTH: 20
<212> TYPE: DNA
<213> ORGANISM: Artificial Sequence
<220> FEATURE:
<223> OTHER INFORMATION: antisense sequence

<400> SEQUENCE: 17
gtcagccatg gtccccsccc                                              20

<210> SEQ ID NO 18
<211> LENGTH: 20
<212> TYPE: DNA
<213> ORGANISM: Artificial Sequence
<220> FEATURE:
<223> OTHER INFORMATION: antisense sequence

<400> SEQUENCE: 18
cgccgtggag tcgttgcccg                                              20

<210> SEQ ID NO 19
<211> LENGTH: 20
<212> TYPE: DNA
<213> ORGANISM: Artificial Sequence
<220> FEATURE:
<223> OTHER INFORMATION: antisense sequence

<400> SEQUENCE: 19
tcaaatggag gctgcccggc                                              20

<210> SEQ ID NO 20
<211> LENGTH: 20
<212> TYPE: DNA
<213> ORGANISM: Artificial Sequence
```

```
<220> FEATURE:
<223> OTHER INFORMATION: antisense sequence

<400> SEQUENCE: 20
tggaatcaga cacaagccgt                                                    20

<210> SEQ ID NO 21
<211> LENGTH: 18
<212> TYPE: DNA
<213> ORGANISM: Artificial Sequence
<220> FEATURE:
<223> OTHER INFORMATION: antisense sequence

<400> SEQUENCE: 21
ttctcgctgg tgagtttc                                                      18

<210> SEQ ID NO 22
<211> LENGTH: 17
<212> TYPE: DNA
<213> ORGANISM: Artificial Sequence
<220> FEATURE:
<223> OTHER INFORMATION: antisense sequence

<400> SEQUENCE: 22
tctcgctggt gagtttc                                                       17

<210> SEQ ID NO 23
<211> LENGTH: 20
<212> TYPE: DNA
<213> ORGANISM: Artificial Sequence
<220> FEATURE:
<223> OTHER INFORMATION: control sequence

<400> SEQUENCE: 23
ggttttacca tcggttctgg                                                    20

<210> SEQ ID NO 24
<211> LENGTH: 2245
<212> TYPE: DNA
<213> ORGANISM: Homo sapiens
<220> FEATURE:
<221> NAME/KEY: CDS
<222> LOCATION: (28)..(2046)
<300> PUBLICATION INFORMATION:
<303> JOURNAL: Nucleic Acids Res.
<304> VOLUME: 18
<305> ISSUE: 8
<306> PAGES: 2183
<307> DATE: 1990-04-25
<308> DATABASE ACCESSION NUMBER: X52479/Genbank
<309> DATABASE ENTRY DATE: 1993-09-12

<400> SEQUENCE: 24
ggagcaagag gtggttgggg ggggacc atg gct gac gtt ttc ccg ggc aac gac        54
                              Met Ala Asp Val Phe Pro Gly Asn Asp
                                1               5 tcc acg gcg tct cag gac gtg gcc aac cgc ttc gcc cgc aaa ggg gcg         102
Ser Thr Ala Ser Gln Asp Val Ala Asn Arg Phe Ala Arg Lys Gly Ala
 10                  15                  20                  25 ctg agg cag aag aac gtg cac gag gtg aag gac cac aaa ttc atc gcg         150
Leu Arg Gln Lys Asn Val His Glu Val Lys Asp His Lys Phe Ile Ala
                 30                  35                  40 cgc ttc ttc aag cag ccc acc ttc tgc agc cac tgc acc gac ttc atc         198
Arg Phe Phe Lys Gln Pro Thr Phe Cys Ser His Cys Thr Asp Phe Ile
             45                  50                  55 tgg ggg ttt ggg aaa caa ggc ttc cag tgc caa gtt tgc tgt ttt gtg         246
```

```
Trp Gly Phe Gly Lys Gln Gly Phe Gln Cys Gln Val Cys Cys Phe Val
        60              65              70 gtc cac aag agg tgc cat gaa ttt gtt act ttt tct tgt ccg ggt gcg      294
Val His Lys Arg Cys His Glu Phe Val Thr Phe Ser Cys Pro Gly Ala
    75              80              85 gat aag gga ccc gac act gat gac ccc agg agc aag cac aag ttc aaa      342
Asp Lys Gly Pro Asp Thr Asp Asp Pro Arg Ser Lys His Lys Phe Lys
90              95              100             105 atc cac act tac gga agc ccc acc ttc tgc gat cac tgt ggg tca ctg      390
Ile His Thr Tyr Gly Ser Pro Thr Phe Cys Asp His Cys Gly Ser Leu
            110             115             120 ctc tat gga ctt atc cat caa ggg atg aaa tgt gac acc tgc gat atg      438
Leu Tyr Gly Leu Ile His Gln Gly Met Lys Cys Asp Thr Cys Asp Met
        125             130             135 aac gtt cac aag caa tgc gtc atc aat gtc ccc agc ctc tgc gga atg      486
Asn Val His Lys Gln Cys Val Ile Asn Val Pro Ser Leu Cys Gly Met
    140             145             150 gat cac act gag aag agg ggg cgg att tac cta aag gct gag gtt gct      534
Asp His Thr Glu Lys Arg Gly Arg Ile Tyr Leu Lys Ala Glu Val Ala
155             160             165 gat gaa aag ctc cat gtc aca gta cga gat gca aaa aat cta atc cct      582
Asp Glu Lys Leu His Val Thr Val Arg Asp Ala Lys Asn Leu Ile Pro
170             175             180             185 atg gat cca aac ggg ctt tca gat cct tat gtg aag ctg aaa ctt att      630
Met Asp Pro Asn Gly Leu Ser Asp Pro Tyr Val Lys Leu Lys Leu Ile
            190             195             200 cct gat ccc aag aat gaa agc aag caa aaa acc aaa acc atc cgc tcc      678
Pro Asp Pro Lys Asn Glu Ser Lys Gln Lys Thr Lys Thr Ile Arg Ser
        205             210             215 aca cta aat ccg cag tgg aat gag tcc ttt aca ttc aaa ttg aaa cct      726
Thr Leu Asn Pro Gln Trp Asn Glu Ser Phe Thr Phe Lys Leu Lys Pro
    220             225             230 tca gac aaa gac cga cga ctg tct gta gaa atc tgg gac tgg gat cga      774
Ser Asp Lys Asp Arg Arg Leu Ser Val Glu Ile Trp Asp Trp Asp Arg
235             240             245 aca aca agg aat gac ttc atg gga tcc ctt tcc ttt gga gtt tcg gag      822
Thr Thr Arg Asn Asp Phe Met Gly Ser Leu Ser Phe Gly Val Ser Glu
250             255             260             265 ctg atg aag atg ccg gcc agt gga tgg tac aag ttg ctt aac caa gaa      870
Leu Met Lys Met Pro Ala Ser Gly Trp Tyr Lys Leu Leu Asn Gln Glu
            270             275             280 gaa ggt gag tac tac aac gta ccc att ccg gaa ggg gac gag gaa gga      918
Glu Gly Glu Tyr Tyr Asn Val Pro Ile Pro Glu Gly Asp Glu Glu Gly
        285             290             295 aac atg gaa ctc agg cag aaa ttc gag aaa gcc aaa ctt ggc cct gct      966
Asn Met Glu Leu Arg Gln Lys Phe Glu Lys Ala Lys Leu Gly Pro Ala
    300             305             310 ggc aac aaa gtc atc agt ccc tct gaa gac agg aaa caa cct tcc aac     1014
Gly Asn Lys Val Ile Ser Pro Ser Glu Asp Arg Lys Gln Pro Ser Asn
315             320             325 aac ctt gac cga gtg aaa ctc acg gac ttc aat ttc ctc atg gtg ttg     1062
Asn Leu Asp Arg Val Lys Leu Thr Asp Phe Asn Phe Leu Met Val Leu
330             335             340             345 gga aag ggg agt ttt gga aag gtg atg ctt gcc gac agg aag ggc aca     1110
Gly Lys Gly Ser Phe Gly Lys Val Met Leu Ala Asp Arg Lys Gly Thr
            350             355             360 gaa gaa ctg tat gca atc aaa atc ctg aag aag gat gtg gtg att cag     1158
Glu Glu Leu Tyr Ala Ile Lys Ile Leu Lys Lys Asp Val Val Ile Gln
        365             370             375
```

-continued

| | |
|---|---|
| gat gat gac gtg gag tgc acc atg gta gaa aag cga gtc ttg gcc ctg<br>Asp Asp Asp Val Glu Cys Thr Met Val Glu Lys Arg Val Leu Ala Leu<br>380                      385                      390 | 1206 |
| ctt gac aaa ccc ccg ttc ttg acg cag ctg cac tcc tgc ttc cag aca<br>Leu Asp Lys Pro Pro Phe Leu Thr Gln Leu His Ser Cys Phe Gln Thr<br>395                      400                      405 | 1254 |
| gtg gat cgg ctg tac ttc gtc atg gaa tat gtc aac ggt ggg gac ctc<br>Val Asp Arg Leu Tyr Phe Val Met Glu Tyr Val Asn Gly Gly Asp Leu<br>410                      415                      420                      425 | 1302 |
| atg tac cac att cag caa gta gga aaa ttt aag gaa cca caa gca gta<br>Met Tyr His Ile Gln Gln Val Gly Lys Phe Lys Glu Pro Gln Ala Val<br>                    430                      435                      440 | 1350 |
| ttc tat gcg gca gag att tcc atc gga ttg ttc ttt ctt cat aaa aga<br>Phe Tyr Ala Ala Glu Ile Ser Ile Gly Leu Phe Phe Leu His Lys Arg<br>                    445                      450                      455 | 1398 |
| gga atc att tat agg gat ctg aag tta gat aac gtc atg ttg gat tca<br>Gly Ile Ile Tyr Arg Asp Leu Lys Leu Asp Asn Val Met Leu Asp Ser<br>                    460                      465                      470 | 1446 |
| gaa gga cat atc aaa att gct gac ttt ggg atg tgc aag gaa cac atg<br>Glu Gly His Ile Lys Ile Ala Asp Phe Gly Met Cys Lys Glu His Met<br>475                      480                      485 | 1494 |
| atg gat gga gtc acg acc agg acc ttc tgt ggg act cca gat tat atc<br>Met Asp Gly Val Thr Thr Arg Thr Phe Cys Gly Thr Pro Asp Tyr Ile<br>490                      495                      500                      505 | 1542 |
| gcc cca gag ata atc gct tat cag ccg tat gga aaa tct gtg gac tgg<br>Ala Pro Glu Ile Ile Ala Tyr Gln Pro Tyr Gly Lys Ser Val Asp Trp<br>                    510                      515                      520 | 1590 |
| tgg gcc tat ggc gtc ctg ttg tat gaa atg ctt gcc ggg cag cct cca<br>Trp Ala Tyr Gly Val Leu Leu Tyr Glu Met Leu Ala Gly Gln Pro Pro<br>                    525                      530                      535 | 1638 |
| ttt gat ggt gaa gat gaa gac gag cta ttt cag tct atc atg gag cac<br>Phe Asp Gly Glu Asp Glu Asp Glu Leu Phe Gln Ser Ile Met Glu His<br>540                      545                      550 | 1686 |
| aac gtt tcc tat cca aaa tcc ttg tcc aag gag gct gtt tct atc tgc<br>Asn Val Ser Tyr Pro Lys Ser Leu Ser Lys Glu Ala Val Ser Ile Cys<br>555                      560                      565 | 1734 |
| aaa gga ctg atg acc aaa cac cca gcc aag cgg ctg ggc tgt ggg cct<br>Lys Gly Leu Met Thr Lys His Pro Ala Lys Arg Leu Gly Cys Gly Pro<br>570                      575                      580                      585 | 1782 |
| gag ggg gag agg gac gtg aga gag cat gcc ttc ttc cgg agg atc gac<br>Glu Gly Glu Arg Asp Val Arg Glu His Ala Phe Phe Arg Arg Ile Asp<br>                    590                      595                      600 | 1830 |
| tgg gaa aaa ctg gag aac agg gag atc cag cca cca ttc aag ccc aaa<br>Trp Glu Lys Leu Glu Asn Arg Glu Ile Gln Pro Pro Phe Lys Pro Lys<br>                    605                      610                      615 | 1878 |
| gtg tgt ggc aaa gga gca gag aac ttt gac aag ttc ttc aca cga gga<br>Val Cys Gly Lys Gly Ala Glu Asn Phe Asp Lys Phe Phe Thr Arg Gly<br>                    620                      625                      630 | 1926 |
| cag ccc gtc tta aca cca cct gat cag ctg gtt att gct aac ata gac<br>Gln Pro Val Leu Thr Pro Pro Asp Gln Leu Val Ile Ala Asn Ile Asp<br>635                      640                      645 | 1974 |
| cag tct gat ttt gaa ggg ttc tcg tat gtc aac ccc cag ttt gtg cac<br>Gln Ser Asp Phe Glu Gly Phe Ser Tyr Val Asn Pro Gln Phe Val His<br>650                      655                      660                      665 | 2022 |
| ccc atc tta cag agt gca gta tga aactcaccag cgagaacaaa cacctcccca<br>Pro Ile Leu Gln Ser Ala Val<br>                    670 | 2076 |

```
                                          -continued
gcccccagcc ctccccgcag tggaagtgaa tccttaaccc taaaatttta aggccacggc    2136
ttgtgtctga ttccatatgg aggcctgaaa attgtagggt tattagtcca aatgtgatca    2196
actgttcagg gtctctctct tacaaccaag aacattatct tagtggaag               2245
```

MODULATION OF C-JUN USING INHIBITORS OF PROTEIN KINASE C

FIELD OF THE INVENTION

This invention relates to therapies, diagnostics, and research reagents for disease states which respond to modulation of the expression of c-jun. Included are methods for modulation of c-jun expression with protein kinase C-α-specific inhibitors. In particular, this invention relates to antisense oligonucleotides specifically hybridizable with nucleic acids relating to protein kinase C-α. Such oligonucleotides have been found to modulate the expression of protein kinase C-α and of c-jun.

BACKGROUND OF THE INVENTION

The phosphorylation of proteins plays a key role in the transduction of extracellular signals into the cell. The enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells (Gescher et al., *Anti-Cancer Drug Design* 4:93–105 (1989)). Phorbols capable of tumor production can mimic the effect of DAG in activating PKC, suggesting that these tumor promoters act through PKC and that activation of this enzyme is at least partially responsible for the resulting tumorigenesis (Parker et al., *Science* 233:853–866 (1986)).

A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs (Gescher, A. and Dale, I. L., *Anti-Cancer Drug Design*, 4:93–105 (1989)).

PKC is not a single enzyme, but a family of enzymes. At the present time at least seven isoforms (isozymes) of PKC have been identified: isoforms α, β, and γ have been purified to homogeneity, and isoforms δ, ε, ζ and η have been identified by molecular cloning. These isozymes have distinct patterns of tissue and organ localization (see Nishizuka, *Nature*, 334:661–665 (1988) for review) and may serve different physiological functions. For example, PKC-γ seems to be expressed only in the central nervous system. PKC-α and -β are expressed in most tissues, but have different patterns of expression in different cell types. For example, both PKC-α and PKC-β are expressed in, and have been purified from, human epidermis. While PKC-α has been detected mainly in keratinocytes of the basal layers of the epidermis, PKC-β is found mainly in the middle layers of the epidermis and Langerhans cells. PKC-η has been found predominantly in the skin and lungs, with levels of expression much higher in these tissues than in the brain. This is in contrast to other members of the PKC family which tend to be most abundantly expressed in the brain (Osada et al., *J Biol. Chem.* 265:22434–22440 (1990)).

It is presently believed that different PKC isozymes may be involved in various disease processes depending on the organ or tissue in which they are expressed. For example, in psoriatic lesions there is an alteration in the ratio between PKC-α and PKC-β, with preferential loss of PKC-β compared to normal skin (Hegemann, L. and G. Mahrle, *Pharmacology of the Skin*, H. Mukhtar, ed., p. 357–368, CRC Press, Boca Raton, Fla., 1992).

One of the biological targets of PKC kinase activity is the c-jun protein encoded by the proto-oncogene c-jun. The c-jun protein is a major component of the AP-1 transcription factor (Bohmarm, D., et al., *Science*, 1987, 238, 1386–1392). Activation of protein kinase C results in dephosphorylation of the latent, phosphorylated form of c-jun protein, and subsequently, increased AP-1 activity (Boyle, W. J., et al., *Cell*, 1991, 8, 573–584).

Increased c-jun activity is associated with a wide variety of cancers and other diseases and conditions. Overexpression of c-jun has been associated with cancers including bladder carcinoma (Skopelitou, A., et al., *Eur. Urol.*, 1997, 31, 464–471), lung carcinoma (Volm, M., et al., *Clin. Exp. Metastasis*, 1994, 12, 329–334), high-grade osteosarcomas (Franchi, A., et al., *Virchows Arch.*, 1998, 432, 515–519), ovarian carcinoma (Spinner, D. M., et al., *Int. J. Cancer*, 1995, 63, 423–427), and tumors associated with the central nervous system, including medulloblastomas, neuroblastomas, astrocytomas and glioblastomas (Ferrer, I., et al., *Neurosci. Lett.*, 1996, 214, 49–52). Overexpression of c-jun is also associated with Alzheimer's disease (Anderson, A. J., et al., *J. Neurosci.*, 1996, 16, 1710–1719), while constitutive expression of c-jun is associated with rheumatoid arthritis (Herlitzka, D. S., et al., *Ann. Rheum. Dis.*, 1996, 55, 298–304).

In the present invention, it has been determined that PKC-α is the isozyme associated with modulation of c-jun expression. It is believed that modulation of PKC-α expression will also aid in the treatment of the cancers and other diseases associated with c-jun.

Numerous compounds have been identified as PKC inhibitors (see Hidaka and Hagiwara, *Trends in Pharm. Sci.* 8:162–164 (1987) for review), though not all of these inhibit PKC specifically. The quinoline sulfonamide derivatives such as 1-(5-isoquinolinesulfonyl)-2-methylpiperazine (H-7) inhibit PKC at micromolar concentrations, though they exhibit similar enzyme inhibition kinetics for PKC and the cAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases (Gescher, *Anti-Cancer Drug Design* 4:93–105 (1989)). Certain ceramides and sphingosine derivatives have been shown to have PKC inhibitory activity and to have promise for therapeutic uses, however, there remains a long-felt need for specific inhibitors of the enzymes.

Inhibitors of PKC may inhibit the activity or the synthesis (i.e. expression) of PKC-α. Specific inhibitors of the PKC-α isozyme include chemical compounds, monoclonal antibodies, protein fragments and antisense oligonucleotides. Go-6976 has been used as a specific PKC-α inhibitor to study the role of this enzyme in Alzheimer's disease (Benussi, L., et al., *Neurosci. Lett.*, 1998, 240, 97–101), although others suggest that this compound is specific for both the α and β1 isoforms (La Porta, Calif., et al., *Br. J. Cancer*, 1998, 78, 1283–1287). Isozyme-specific monoclonal antibodies have been used to study their role in various cellular processes (Liao, L. and Jaken., S., *Cell Growth Differ.*, 1993, 4, 309–316; Chen, C. C., et al., *Mol. Pharmacol.*, 1995, 48, 39–47). Parissenti, A. M., et al. (*J.*

Biol. Chem., 1998, 273, 8940–8945) used PKC-α fusion proteins and deletion protein as specific PKC-α inhibitors. Godson et al. (J. Biol. Chem., 1993, 268, 11946–11950) disclosed use of stable transfection of antisense PKC-α cDNA in cytomegalovirus promotor-based expression vectors to specifically decrease expression of PKC-α protein by approximately 70%. It was demonstrated that this inhibition caused a loss of phospholipase $A_2$-mediated arachidonic acid release in response to the phorbol ester PMA. Attempts by the same researchers at inhibiting PKC activity with oligodeoxynucleotides were ultimately unsuccessful due to degradation of oligonucleotides. Ahmad et al. disclose that transfection of the human glioblastoma cell line, U-87, with vectors expressing antisense RNA to PKCα inhibits growth of the glioblastoma cells in vitro and in vivo. Ahmad et al., Neurosurg., 1994, 35, 904–908.

Fung, H., et al. (Cancer Res., 1997, 57, 3101–3105) purport to show that inhibition of PKC-α prevents asbestos-induced c-fos and c-jun expression. They demonstrate that PKC-α is the major isoform is a mesothelial cell line and that a general PKC inhibitor reduces c-fos and c-jun expression.

Thus, there is the need for improved methods and compositions for specific PKC-α inhibitors especially in modulation of c-jun expression.

BRIEF DESCRIPTION OF THE DRAWINGS

FIG. 9A shows oligonucleotides 6632, 6653 and 6665.

FIG. 9B shows oligonucleotides 3521 (for comparison), 7082, 7083 and 7084. Hatched bars represent the 8.5 kb transcript, plain bars represent the 4.0 kb transcript.

SUMMARY OF THE INVENTION

Figure 1A:
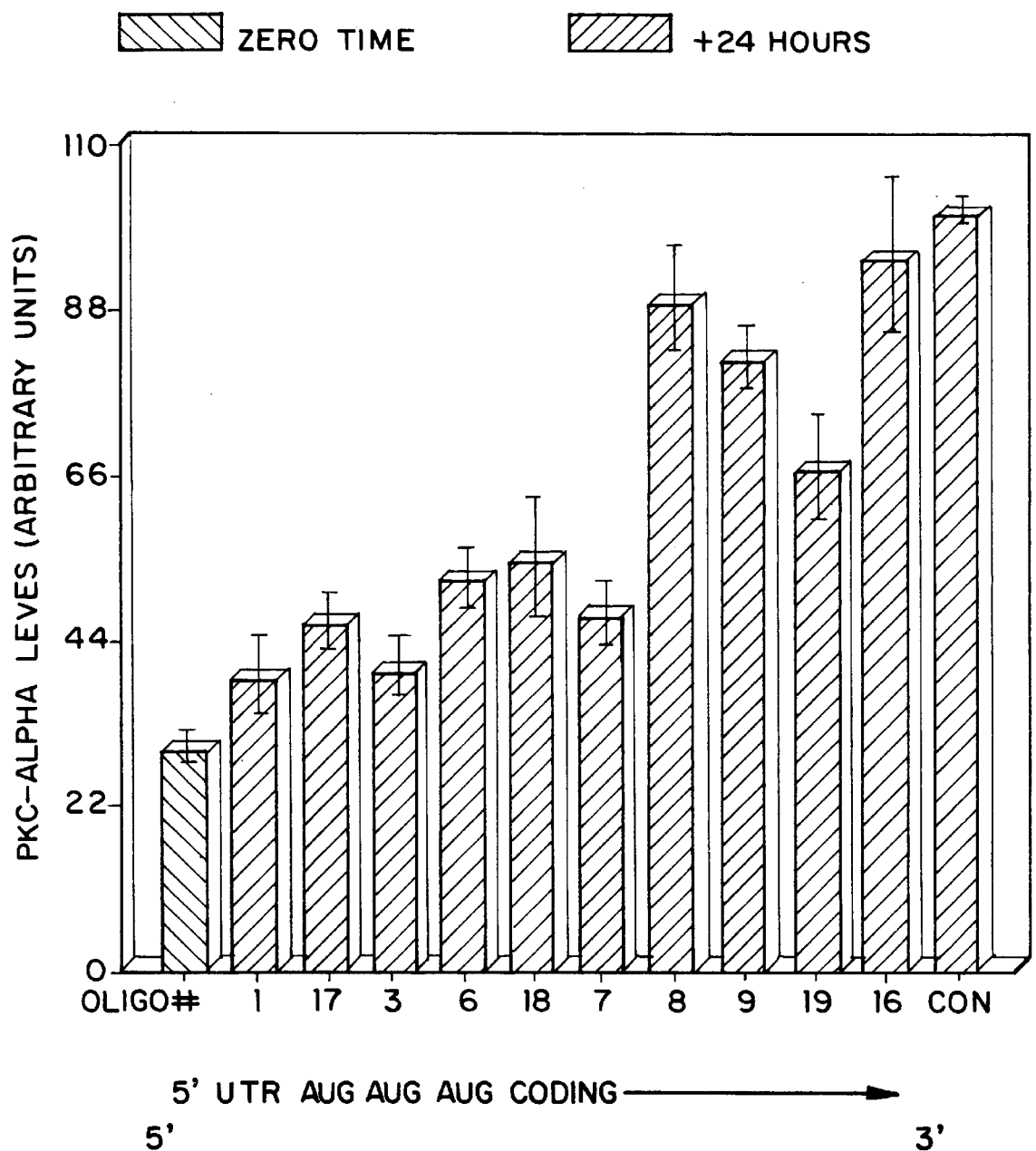
FIGS. 1(a) and 1(b) are graphical depictions of the effects on PKC expression of antisense oligonucleotides hybridizable with PKC-α. Oligonucleotides are arranged by PKC target region, 5' to 3'.

Provided in the invention are methods and compounds directed to the modulation of c-jun using specific inhibitors of PKC-α. In one preferred embodiment, the specific inhibitor is an antisense oligonucleotide capable of hybridizing to PKC-α.

In accordance with preferred embodiments, the oligonucleotides comprise one or more chemical modifications which convey some desired characteristic such as improved target affinity, cellular uptake or stability in the presence of cellular nucleases. Examples of modifications having such utility are modifications at the 2' position of the nucleotide sugar and phosphorothioate and other modifications of the oligonucleotide backbone.

Other aspects of the invention are directed to methods for diagnostics and therapeutics of animals suspected of having a disease associated with c-jun.

Such methods comprise contacting cells or tissues suspected of containing said gene with inhibitors of PKC-α in accordance with the invention. In the context of this invention, to "contact" tissues or cells with an inhibitor or inhibitors means to add the inhibitor(s), usually in a liquid carrier, to a cell suspension or tissue sample, either in vitro or ex vivo, or to administer the inhibitor(s) to cells or tissues within an animal.

DETAILED DESCRIPTION OF PREFERRED EMBODIMENTS

The present invention uses inhibitors of PKC-α to modulate c-jun expression. These inhibitors include chemical compounds, such as Go-6976, monoclonal antibodies, protein fragments and antisense oligonucleotides. Modulation of c-jun expression may be used as a treatment or diagnostic for diseases such as various cancers, Alzheimer's disease and rheumatoid arthritis. Cancers amenable to treatment or diagnosis with this invention include cancers of the bladder, bone, lung, ovary or central nervous system. In a preferred embodiment, the inhibitor of PKC-α is an antisense oligonucleotide specifically hybridizable with nucleic acid(s) encoding PKC-α.

Oligonucleotides have been employed as therapeutic moieties for the treatment of disease states in animals and man. For example, workers in the field have now identified antisense, triplex and other oligonucleotide compositions which are capable of modulating expression of genes implicated in viral, fungal and metabolic diseases.

Antisense oligonucleotides have been safely administered to humans and clinical trials of numerous antisense oligonucleotide drugs, targeted both to viral and cellular gene products, are presently underway. The phosphorothioate oligonucleotide drug, Vitravene™, has been approved by the FDA for use against cytomegalovirus retinitis in AIDS patients. *BioWorld Today*, Aug. 28, 1998. It is thus established that oligonucleotides can be useful therapeutic instrumentalities and can be configured to be useful in treatment regimes for treatment of cells and animal subjects, especially humans.

As used herein, the terms "target nucleic acid" and "nucleic acid encoding PKC-α" encompass DNA encoding PKC-α, RNA (including pre-mRNA and mRNA) transcribed from such DNA, and also CDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of PKC-α, In the context of the present invention, "modulation" means either an increase (stimulation) or a decrease (inhibition) in the expression of a gene. In the context of the present invention, inhibition is the preferred form of modulation of gene expression and mRNA is a preferred target. This modulation can be measured in ways which are routine in the art, for example by northern blot assay of mRNA expression, reverse transcriptase PCR, or by western blot, ELISA or immunoprecipitation assay of protein expression.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding PKC-α. The targeting process also includes determination of a site or sites within this gene for the antisense interaction to occur such that the desired effect, e.g., detection or modulation of expression of the protein, will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intronl/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to fimction in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding PKC-α, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal fimction of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

The overall effect of interference with mRNA function is modulation of expression of PKC-α and, in the context of this invention, ultimately modulation of c-jun expression.

The present invention is also suitable for diagnosing abnormal disease states in tissue or other samples from patients suspected of having a disease such as cancer, Alzheimer's disease or rheumatoid arthritis. The ability of the oligonucleotides of the present invention to inhibit signal transduction may be employed to diagnose such states. A number of assays may be formulated employing the present invention, which assays will commonly comprise contacting a tissue sample with an oligonucleotide of the invention under conditions selected to permit detection and, usually, quantitation of such inhibition.

The oligonucleotides of this invention may also be used for research purposes. For example, the function of a specific gene product in a signaling pathway may be investigated using specific oligonucleotides. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that firther include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their intemucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5'to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is incorporated herein by reference in its entirety.

Preferred modified oligonucleotide backbones that do not include a phosphorus atom therein have backbones that are formed by short chain alkyl or cycloalkyl internucleoside linkages, mixed heteroatom and alkyl or cycloalkyl intemucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is incorporated herein by reference in its entirety.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is incorporated herein by reference in its entirety. Further teaching of PNA compounds can be found in Nielsen et al. (*Science*, 1991, 254, 1497–1500), which is incorporated herein by reference in its entirety.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_2$ON($CH_3$)$_2$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta* 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow.

Other preferred modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is incorporated herein by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-arninoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-arnino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press, each of which is incorporated herein by reference in its entirety. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. Nos. 3,687,808, as well as U.S. Pat. No. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594,121, 5,596,091; 5,614,617; and 5,681,941, each of which is incorporated herein by reference in its entirety.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937), each of which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is incorporated herein by reference in its entirety.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl- substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2CH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2CH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993, which is incorporated herein by reference in its entirety.

For therapeutic or prophylactic treatment, oligonucleotides are administered in accordance with this invention. Oligonucleotide compounds of the invention may be formulated in a pharmaceutical composition, which may include phannaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, ie., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)[Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404, each of which is incorporated herein by reference in its entirety.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylnelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 μg to 100 g per kg of body weight, and may be given once or more daily, weekly, monthly or yearly, or even once every 2 to 20 years. Such dosages are an "amount effective to modulate" c-jun expression. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1

Synthesis of Oligonucleotides

Unmodified oligodeoxynucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides were synthesized using 2'-methoxy β-cyanoethyldiisopropyl-phosphoramidites (Chemgenes, Needham, Md.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides are synthesized as described in Kawasaki et al. (J. Med. Chem. 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl- (DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (Helv. Chim. Acta 1995, 78, 486–506). For ease of synthesis, the last nucleotide may be a deoxynucleotide. 2'-O—$CH_2CH_2OCH_3$ cytosines may be 5-methyl cytosines.

Synthesis of 5-Methyl Cytosine Monomers
2,2'-Anhydro[1-(β-D-arabinofuranosyl)-5-methylridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.
2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150mL) and th e filtrate evaporated. The residue (280 g) was dissolved in $CH_3CN$ (600 mL) and evaporated. A silica gel column (3 kg) was packed in $CH_2Cl_2$/acetone/MeOH (20:5:3) con taining 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.
2-O-Methoxyethel-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was a d ded and the reaction stirred for an additiona 1 one hour. Methanol (170 mL) was then added to stop the rea ction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0. 5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhyd ride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methlcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tic showed the reaction to be approximately 95% complete. The solvent was evaporated and the residue azeotroped with MeOH (200 mL). The residue was dissolved in CHCl$_3$ (700 ML) and extracted with saturated NaHCO$_3$ (2×300 mL) and saturated NaCI (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzyl-2'-O-methoxyethyl-5'-O-dimethoxytrityl-5-methylcytidine-3'-amitide:

N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromato-graphed on a 1.5 kg silica column using EtOAc$^{Hexane}$ (3:1) as the eluting solvent. The pure fractions were combined to give 90.6 g (87%) of the title compound.

5-methyl-2'-deoxycytidine (5-me-C) containing oligo-nucleotides were synthesized according to published methods (Sanghvi et al., *Nucl. Acids Res.* 1993, 21, 3197–3203) using commercially available phosphoramidites (Glen Research, Sterling Va. or ChemGenes, Needham Md.).

2'-O-(dimethylaminooxyethyl) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenysilyl-O$^2$-2'anhydro-5-methyluridine

O$^2$-2'-anhydro-5-methyluridine (Pro. Bio. Sint., Varese, Italy, 100.0 g, 0.416 mmol), dimethylaminopyridine (0.66g, 0.013eq, 0.$^{0054}$mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600mL) and the solution was cooled to −10° C. The resulting crystalline product was collected by filtration, washed with ethyl ether (3×200 mL) and dried (40° C., 1 mm Hg, 24 h) to 149g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. (Alternatively, once the low boiling solvent is gone, the remaining solution can be partitioned between ethyl acetate and water. The product will be in the organic phase.) The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98mmol) was mixed with triphenylphosphine (11.63 g, 44.36mmol) and N-hydroxyphthalimide (7.24 g, 44.36mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenlsilyl-2'-O-[(2-aformadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy) ethyl]-5-methyluridine as white foam (1.95, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyuridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (10 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxtethyl)-5-methyluridine-3'-[(2-cyanoethyl)-N,N-diisopropylphosphoramiditel]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-$N,N,N^1,N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages are synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller), which is incorporated herein by reference in its entirety.

Peptide-nucleic acid (PNA) oligomers are synthesized according to P. E. Nielsen et al. (*Science* 1991, 254, 1497–1500), which is incorporated herein by reference in its entirety.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Example 2

PKC-α Antisense Oligonucleotide Sequences

The oligonucleotides tested are presented in Table 1. Sequence data are from the cDNA sequence published by Finkenzeller et al., *Nucl. Acids Res.*, 1990, 18, 2183; Genbank accession number X52479, SEQ ID NO. 24. The sequence numbers given under the oligonucleotides are relative to the first residue to be sequenced on the cDNA, which is 28 residues upstream of the ATG start codon.

TABLE 1

OLIGONUCLEOTIDES TARGETED TO HUMAN PKC-α

| SEQ ID NO | Sequence | Target | ISIS # |
|---|---|---|---|
| 1 | CCC CAA CCA CCT CTT GCT CC 19 1 | 5' Untranslated | 3520 |
| 2 | GTT CTC GCT GGT GAG TTT CA 2063 2044 | 3' Untranslated | 3521 |

TABLE 1-continued

OLIGONUCLEOTIDES TARGETED TO HUMAN PKC-α

| SEQ ID NO | Sequence | Target | ISIS # |
|---|---|---|---|
| 3 | AAA ACG TCA GCC ATG GTC CC 41 22 | Translation init. codon | 3522 |
| 4 | GGA TTC ACT TCC ACT GCG GG 2109 2090 | 3' Untranslated | 3526 |
| 5 | GAG ACC CTG AAC AGT TGA TC 2211 2192 | 3' Untranslated | 3527 |
| 6 | CCC GGG AAA ACG TCA GCC AT 47 28 | Translation init codon | 3674 |
| 7 | CTG CCT CAG CGC CCC TTT GC 110 91 | Internal (C1) domain | 3682 |
| 8 | AGT CGG TGC AGT GGC TGG AG 193 174 | Internal (C1) domain | 3686 |
| 9 | GCA GAG GCT GGG GAC ATT GA 480 461 | Internal (C1) domain | 3687 |
| 10 | GGG CTG GGG AGG TGT TTG TT 2080 2061 | 3' Untranslated | 3695 |
| 11 | CAC TGC GGG GAG GGC TGG GG 2098 2079 | 3' Untranslated | 3875 |
| 12 | AGC CGT GGC CTT AAA ATT TT 2137 2118 | 3' Untranslated | 3878 |
| 13 | ATT TTC AGG CCT CCA TAT GG 2168 2149 | 3' Untranslated | 3879 |
| 14 | AAG AGA GAG ACC CTG AAC AG 2217 2198 | 3' Untranslated | 3884 |
| 15 | GAT AAT GTT CTT GGT TGT AA 2235 2216 | 3' Untranslated | 3885 |
| 16 | ATG GGG TGC ACA AAC TGG GG 2027 2008 | Internal (C3) domain | 3886 |
| 17 | GTC AGC CAT GGT CCC CCC CC 36 17 | Translation init. codon | 3890 |
| 18 | CGC CGT GGA GTC GTT GCC CG 63 44 | Internal (V1) domain | 3891 |
| 19 | TCA AAT GGA GGC TGC CCG GC 1643 1624 | Internal (C3) domain | 3892 |
| 20 | TGG AAT CAG ACA CAA GCC GT 2151 2132 | 3' Untranslated | 3947 |

Example 3

Cell Culture and Treatment with Phorbol Esters and Oligonucleotides Targeted to PKC-αa PKC protein half-lives have been reported to vary from 6.7 hours to over 24 (Young et al., *Biochem. J.* 244:775–779 (1987); Ballester et al., *J. Biol. Chem.* 15194–15199 (1985)). These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct quence of an increased rate of proteolysis of the kinase with no apparent change in synthetic rate.

We determined that in human lung carcinoma (A549) cells, treatment with the ol ester 12,13-dibutyrate (PDBu), using a modification of the method of Krug et rug et al., *J. Biol. Chem.* 262:11852–11856 (1987)) lowered cellular levels of PKC-α without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.).

Cells were treated with 500 nM PDBu (Sigma Chem. Co., St. Louis, Mo.) for 12–16 hours (overnight). Cells were then washed three times in DME at 37° C., and 1 ml DMA containing 20 μl DOTMA (LIPOFECTIN® reagent, BRL, Bethesda, Md.) was added. Oligonucleotides were added to a concentration of 1 μM and the cells were incubated for a further 4 hours at 37° C.

Cells were washed once in 3 ml DME containing 0.1 mg/ml BSA and a further 2 ml DME containing 0.1 mg/ml BSA was added. Oligonucleotides (1 μM) were added and the cells were incubated at 37° C. for 24 hours.

Cells were washed three times in phosphate-buffered saline (PBS) and cellular proteins were extracted in 120 μl sample buffer (60 mM Tris pH 6.8, 2% SDS, 10% glycerol, 10 mM dithiothreitol) and boiled for 5 minutes. Intracellular levels of PKC-α protein were determined by immunoblotting.

Example 4

Immunoblot Assay for PKC Expression

Cell extracts were electrophoresed on 10% SDS-PAGE mini-gels. The resolved proteins were transferred to Immobilon-P membrane (Millipore, Bedford Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-α (UBI, Lake Placid, N.Y.) diluted to 0.2 μg/ml in TBS containing 0.2% nonfat milk. This was followed by three washes in TBS plus 0.2% nonfat milk. The membrane was then incubated for one hour with $^{125}$I-labelled goat anti-mouse secondary antibody (ICN Radiochemicals, Irvine, Calif.). Membranes were then washed extensively in TBS plus 0.2% nonfat milk. Bands were visualized and quantitated using a Phosphorimager (Molecular Dynamics, Sunnyvale, Calif.). PKC-α appears as a single band with a molecular weight of 80 kD.

Figure 1B:
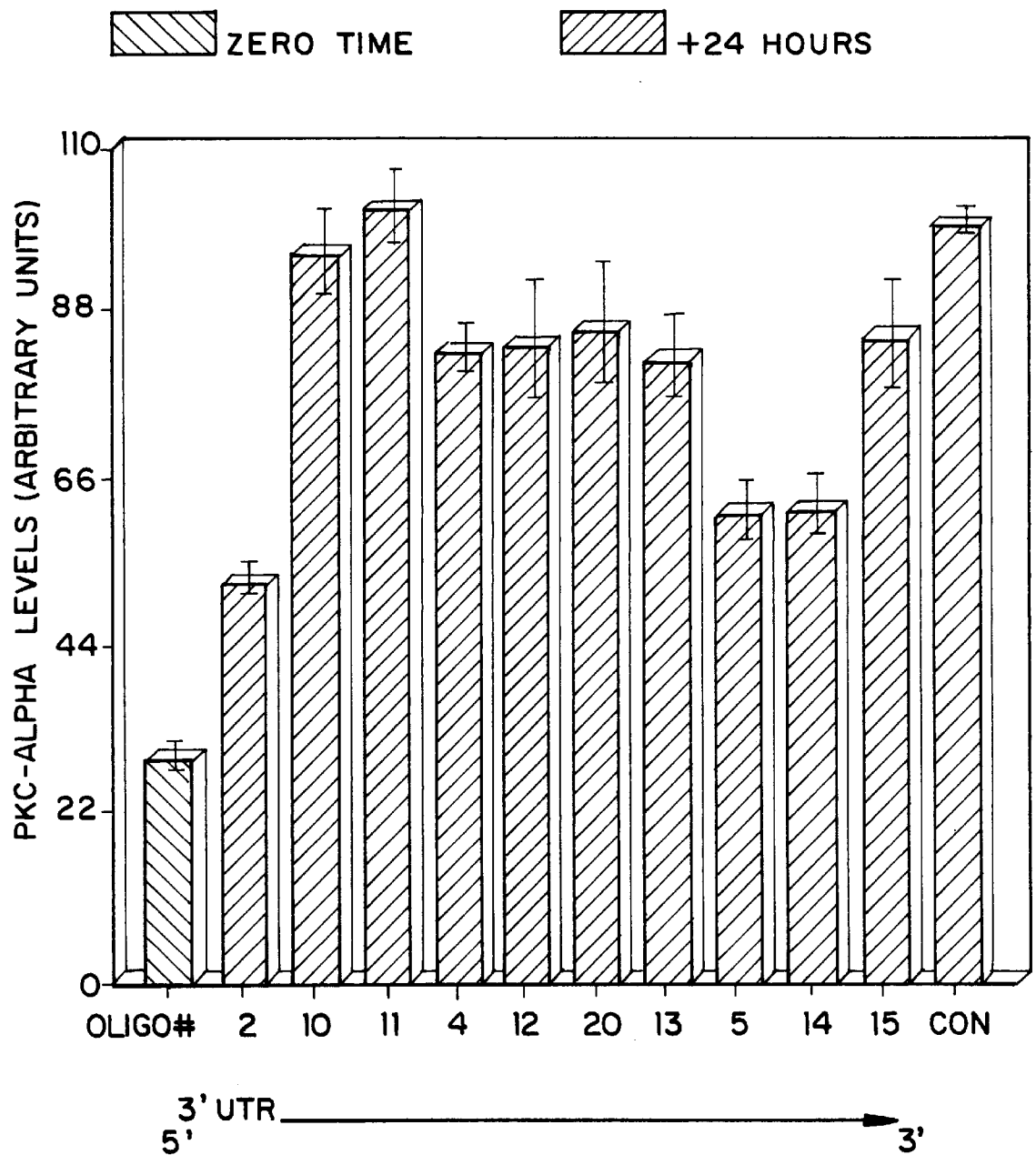

Each oligonucleotide was tested three times, in triplicate, and the results of the experiments were normalized against percentage of protein present as compared to cells which were not treated with oligonucleotide (FIGS. 1a and 1b). The five most effective oligonucleotides target the AUG start codon and regions slightly upstream and downstream from it (Sequence Nos. 1, 3, 17, 7, 6). The next most effective oligonucleotides are targeted toward the 3' untranslated region of the RNA (oligos 2, 5, 14).

Example 5

Figure 2:
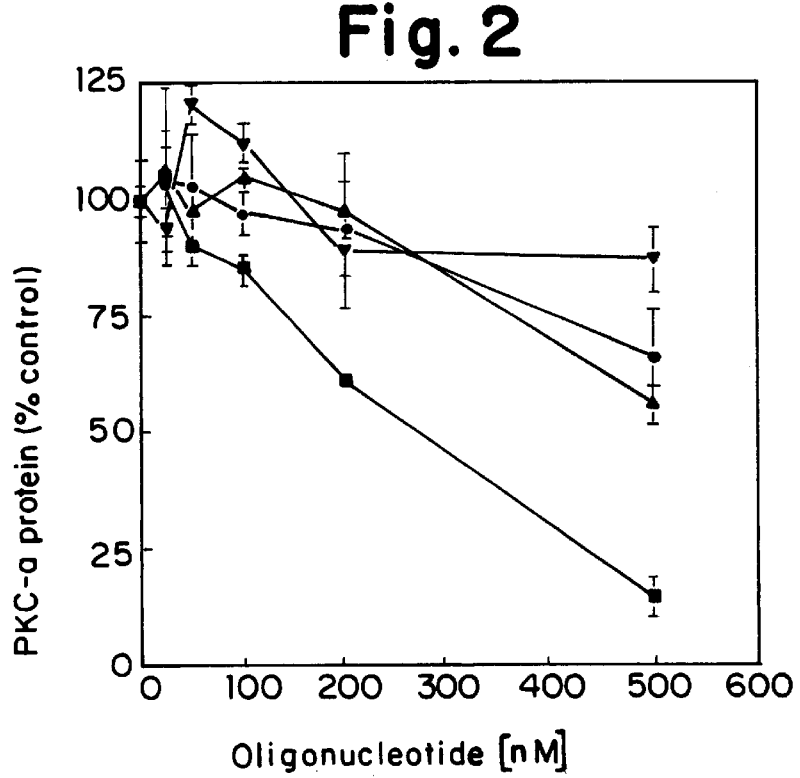
FIG. 2 is a line graph showing dose-dependent reduction of PKC-α protein levels after oligonucleotide treatment of A549 cells. ▼=ISIS 4632; ■=ISIS 4649; ●=ISIS 4636; ▲=ISIS 4648.

Dose Response of Phosphorothioate/2'-O-methyl Oligonucleotide Effects on PKC-α Protein Synthesis A series of phosphorothioate, fully 2'-O-methyl oligonucleotides having SEQ ID NO: 1, 2, 3 and 5 were synthesized. A549 cells were treated with 500 nM PDBu for 18 hours to downregulate PKC-α synthesis, washed to remove PDBu and then treated with oligonucleotide and DOTMA/DOPE cationic liposomes. Medium was replaced after four hours and the cells were allowed to recover for another 20 hours. Proteins were extracted and PKC-α protein levels were determined by immunoblotting as described in Example 3. Results were quantified with a phosphorimager (Molecular Dynamics, Sunnyvale, Calif.) and are shown in FIG. 2 expressed as percent of control (saline treatment). ISIS 4649 (SEQ ID NO: 3; squares) reduced PKC-α protein levels by 85–90% at 500 nM and had an IC50 of approximately 260 nM.

Example 6

Effect of Antisense Oligonucleotides on PKC-α mRNA Levels

Figure 3:
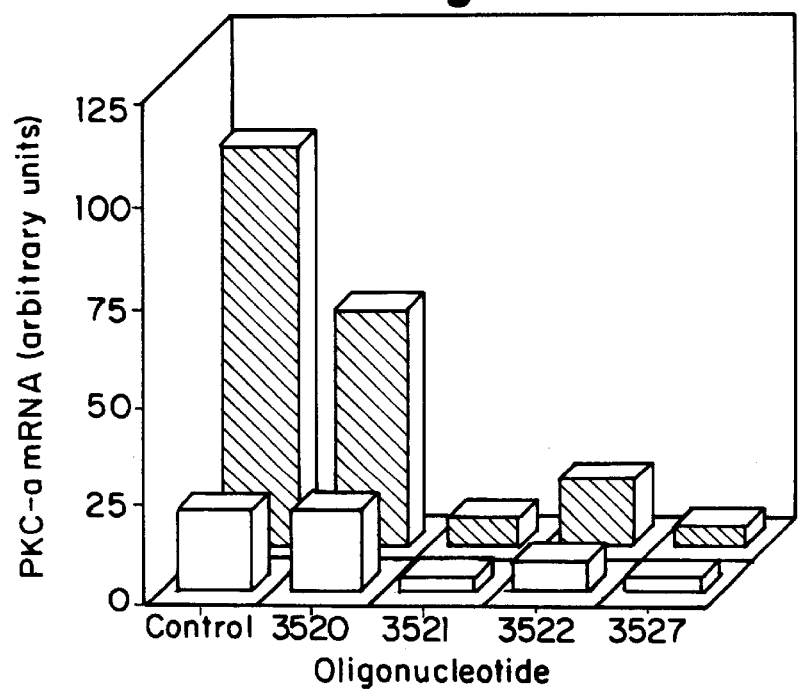
FIG. 3 is a bar graph showing reduction of PKC-α mRNA after treatment of A549 cells with oligonucleotides. Hatched bars represent the 8.5 kb transcript, plain bars represent the 4.0 kb transcript.

A549 cells were treated with phosphorothioate oligonucleotides at 500 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$P radiolabeled PKC-α cDNA probe and then stripped and reprobed with a radiolabeled G3PDH probe to confirm equal RNA loading. Each oligonucleotide (3520, 3521, 3522 and 3527) was used in duplicate. The two major PKC-α transcripts (8.5 kb and 4.0 kb) were examined and quantified with a PhosphorImager (Molecular Dynamics, Sunnyvale, Calif.). Results are shown in FIG. 3. Oligonucleotides 3521 (SEQ ID NO: 2), 3522 (SEQ ID NO: 3) and 3527 (SEQ ID NO: 5) gave better than 50% reduction of PKC-α mRNA levels. Oligonucleotides 3521 and 3527 gave approximately 80% reduction of the smaller transcript and over 90% reduction of the larger transcript.

Example 7

Chimeric (deoxy gapped) 2'-O-methyl Oligonucleotides

Figure 4:
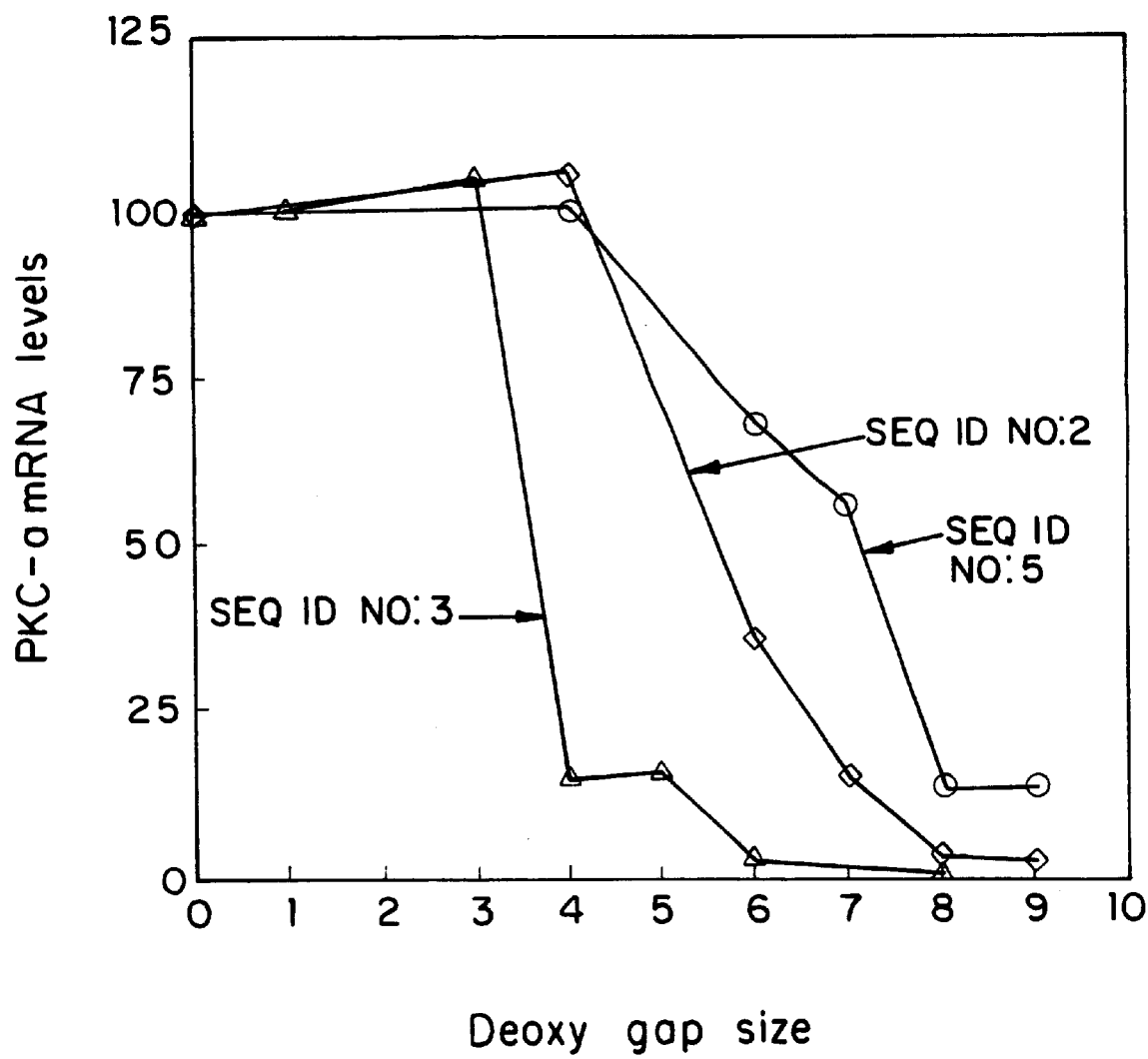
FIG. 4 is a line graph showing the relationship between deoxy gap length and activity of chimeric oligonucleotides against PKC.

Oligonucleotides 3521 (SEQ ID NO: 2), 3522 (SEQ ID NO: 3) and 3527 (SEQ ID NO: 5) were chosen for further study and modification. Oligonucleotides having these sequences were synthesized as uniformly phosphorothioate chimeric oligonucleotides having a centered deoxy gap of various lengths flanked by 2'-O-methylated regions. These oligonucleotides (500 nM concentration) were tested for effects on PKC-α mRNA levels by Northern blot analysis. Results are shown in FIG. 4. Deoxy gaps of eight nucleotides or more gave maximal reduction of PKC-α mRNA levels (both transcripts) in all cases. The oligo-nucleotide having SEQ ID NO: 3 reduced PKC-α mRNA by approximately 83% with a deoxy gap length of four nucleotides, and gave nearly complete reduction of PKC-α mRNA with a deoxy gap length of six or more.

Figure 5:
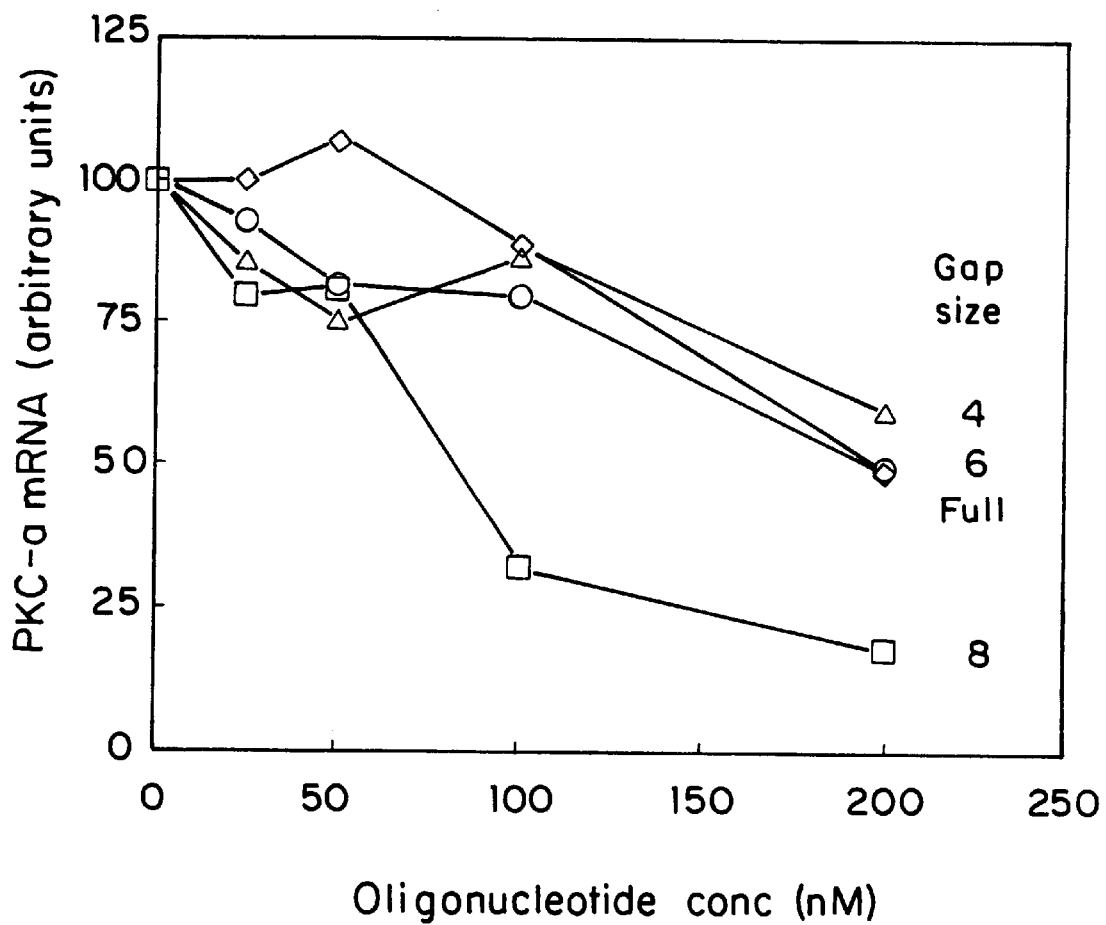
FIG. 5 is a line graph showing dose response curves for chimeric oligonucleotides (all SEQ ID NO: 3) with different deoxy gap lengths.

Dose-response curves for these oligonucleotides are shown in FIG. 5. The 2'-O-methyl chimeric oligonucleotides with four- or six-nucleotide deoxy gaps have an IC50 for PKC-α mRNA reduction (concentration of oligonucleotide needed to give a 50% reduction in PKC-α mRNA levels) of 200–250 nM, as did the full-deoxy oligonucleotide (all are phosphorothioates throughout). The 2'-O-methyl chimeric oligonucleotide with an 8-nucleotide deoxy gap had an IC50 of approximately 85 nM.

Several variations of this chimeric oligonucleotide (SEQ. ID NO: 3) were compared for ability to lower PKC-α mRNA levels. These oligonucleotides are shown in Table 2.

TABLE 2

Chimeric 2'-O-methyl/deoxy P = S oligonucleotides
bold = 2'-O-methyl; s = P = S linkage, o = P = O linkage

| OLIGO # | SEQUENCE | SEQ ID NO: |
|---|---|---|
| 3522 | AsAsAsAsCsGsTsCsAsGsCsCsAsTsGsGsTsCsCsC | 3 |
| 5352 | AsAsAsAsCsGsTsCsAsGsCsCsAsTsGsGsTsCsCsC | 3 |
| 6996 | AoAoAoAoCoGsTsCsAsGsCsCsAsTsGoGoToCoCoC | 3 |
| 7008 | AsAoAoAoCoGsTsCsAsGsCsCsAsTsGoGoToCoCsC | 3 |
| 7024 | AsAoAoAoCoGsToCsAoGsCoCsAsTsGoGoToCoCsC | 3 |

Figure 6:
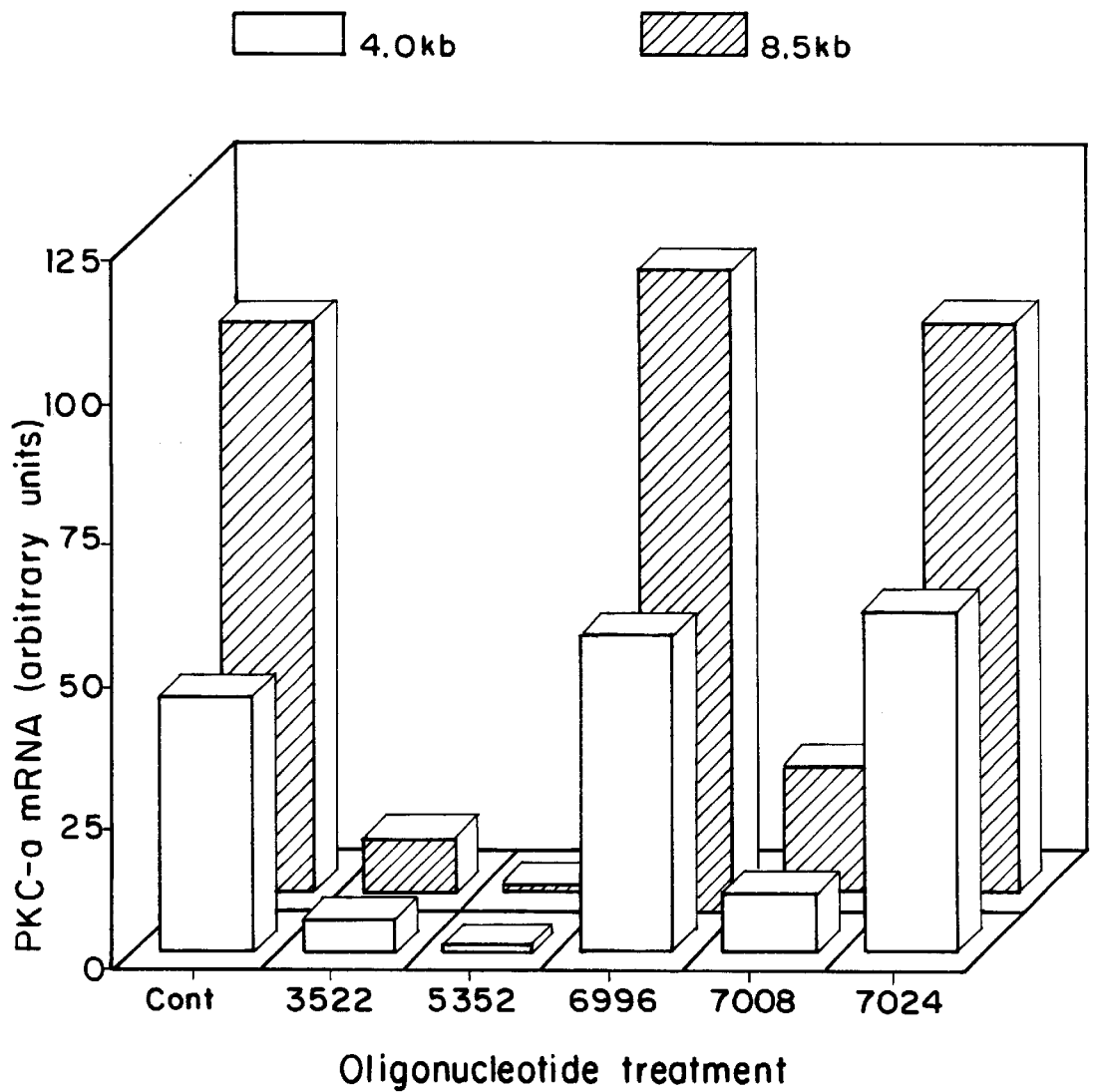
FIG. 6 is a bar graph showing the effects of several 2'-O-methyl chimeric oligonucleotides of SEQ ID NO: 3 on PKC-α mRNA levels. Hatched bars represent the 8.5 kb transcript, plain bars represent the 4.0 kb transcript.

Effects of these oligonucleotides on PKC-α mRNA levels is shown in FIG. 6. Oligonucleotides 7008, 3522 and 5352 show reduction of PKC-α mRNA, with 5352 being most active.

A series of 2'-O-propyl chimeric oligonucleotides was synthesized having SEQ ID NO:3. These oligonucleotides are shown in Table 3.

TABLE 3

Chimeric 2'-O-propyl/deoxy P = S oligonucleotides
bold = 2'-O-propyl; s = P = S linkage, o = P = O linkage

| OLIGO # | SEQUENCE | SEQ ID NO: |
|---|---|---|
| 7199 | AsAsAsAsCsGsTsCsAsGsCsCsAsTsGsGsTsCsCsC | 3 |
| 7273 | AoAoAoAoCoGsTsCsAsGsCsCsAsTsGoGoToCoCoC | 3 |
| 7294 | AsA0AoAoCoGsTsCsAsGsCsCsAsTsGoGoToCoCsC | 3 |
| 7295 | AsAoAoAoCoGsToCsAoGsCoCsAsTsGoGoToCoCsC | 3 |

Figure 7:
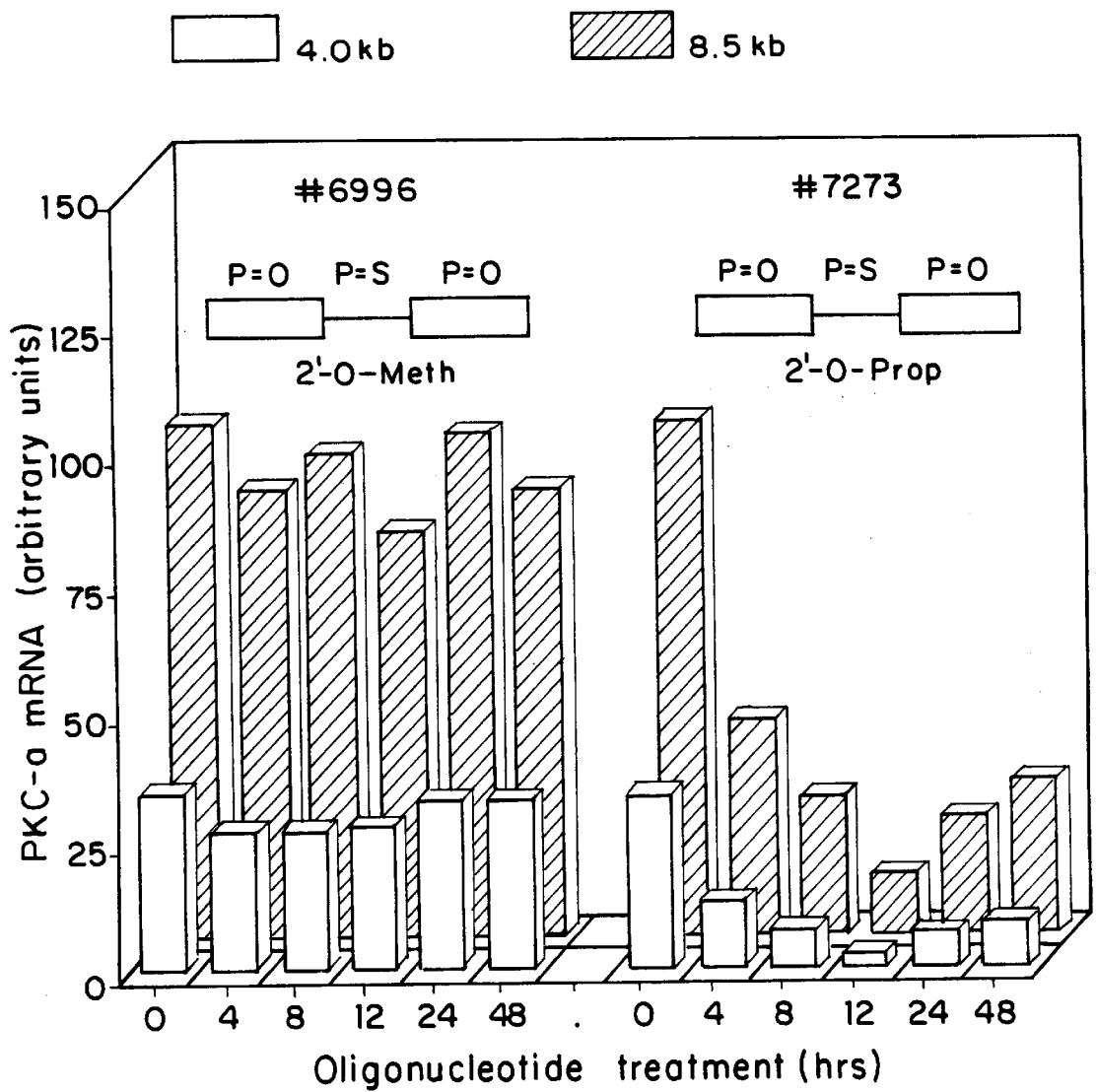
FIG. 7 is a bar graph and diagram showing the effects of several 2'-O-methyl and 2'-O-propyl chimeric oligonucleotides (6996, 7273) of SEQ ID NO: 3 on PKC-α MRNA levels. Hatched bars represent the 8.5 kb transcript, plain bars represent the 4.0 kb transcript.
Figure 8:
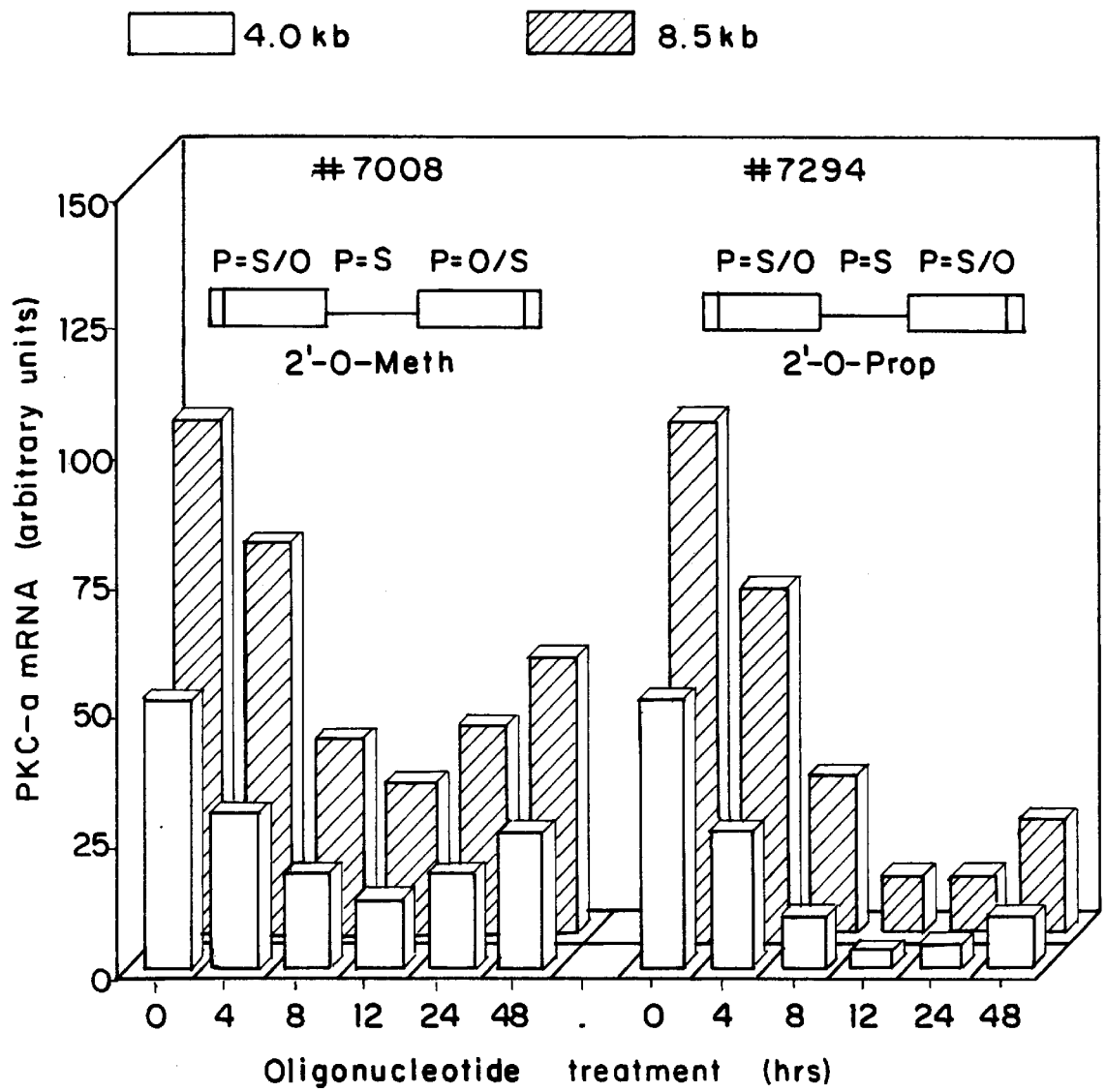
FIG. 8 is a bar graph and diagram showing the effects of additional 2'-O-methyl and 2'-O-propyl chimeric oligonucleotides (7008, 7294) of SEQ ID NO: 3 on PKC-α MRNA levels. Hatched bars represent the 8.5 kb transcript, plain bars represent the 4.0 kb transcript.

These 2'-O-propyl chimeric oligonucleotides were compared to the 2'-O-methyl chimeric oligonucleotides. Oligonucleotides 7273 and 7294 were more active than their 2'-O-methyl counterparts at lowering PKC-α PRNA levels. This is shown in FIGS. 7 and 8.

Example 8

Additional Oligonucleotides Which Decrease PKC-α mRNA

Additional phosphorothioate oligonucleotides targeted to the human PKC-α 3' slated region were designed and synthesized. These sequences are shown in Table 4

TABLE 4

Chimeric 2'-O-propyl/deoxy P = S oligonucleotides targeted to PKC-α 3'-UTR
bold = 2'-O-propyl; s = P = S linkage, o = P = O linkage

| OLIGO # | SEQUENCE | SEQ ID NO: |
|---|---|---|
| 6632 | TsTsCs TsCsGs CsTsGs GsTsGs AsGsTs TsTsC | 21 |
| 6653 | TsTsCs TsCsGs CsTsGs GsTsGs AsGsTs TsTsC | 21 |
| 6665 | ToToCo TsCsGs CsTsGs GsTsGs AsGsTo ToToC | 21 |
| 7082 | TsCsTs CsGsCs TsGsGs TsGsAs GsTsTs TsC | 22 |
| 7083 | TsCsTs CsGsCs TsGsGs TsGsAs GsTsTs TsC | 22 |
| 7084 | ToCoTo CsGsCs TsGsGs TsGsAs GsToTo ToC | 22 |

Figure 9A:
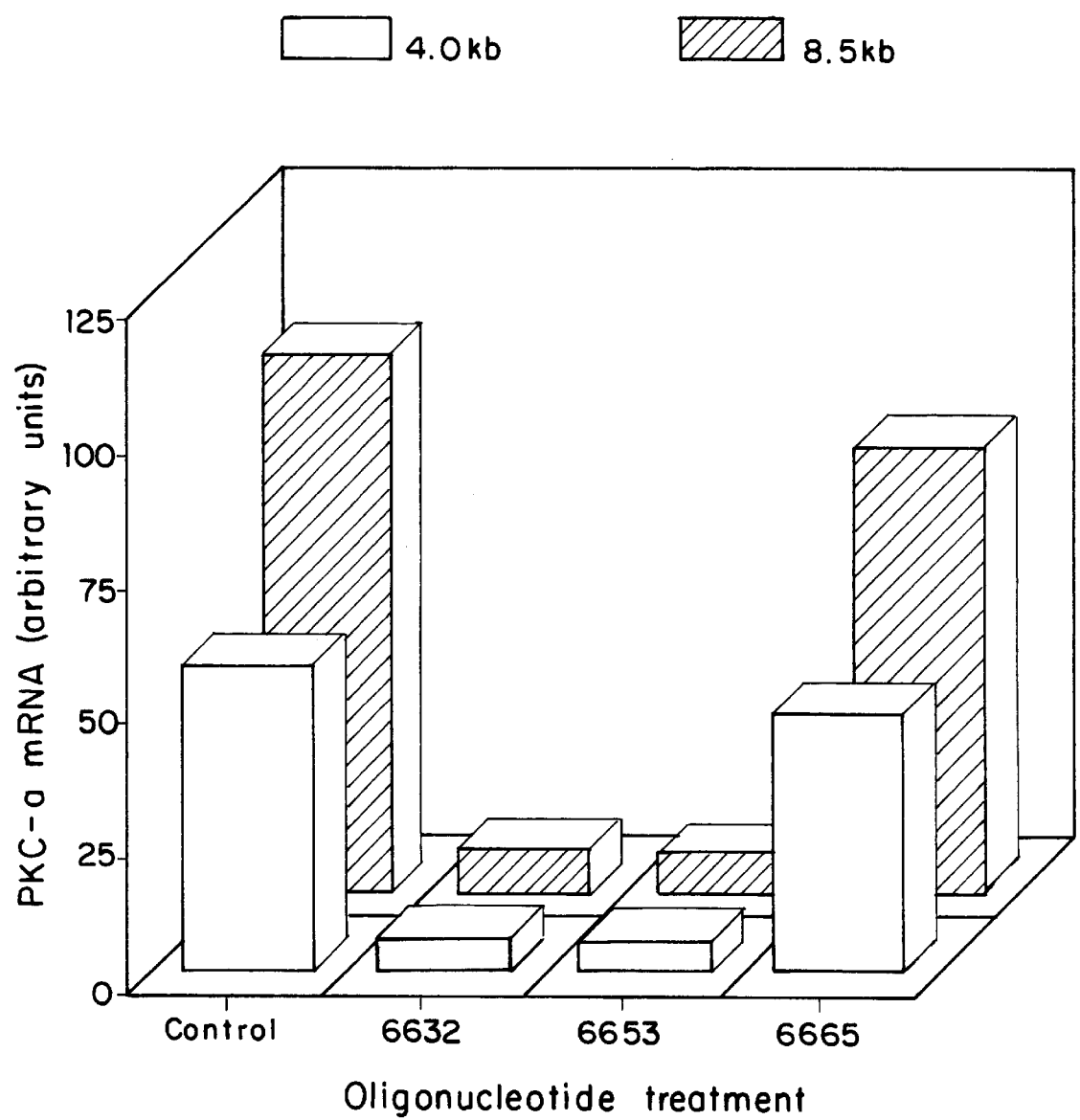
FIGS. 9A–9B are a set of bar graphs showing the effect of additional oligonucleotides on PKC-α mRNA levels.
Figure 9B:
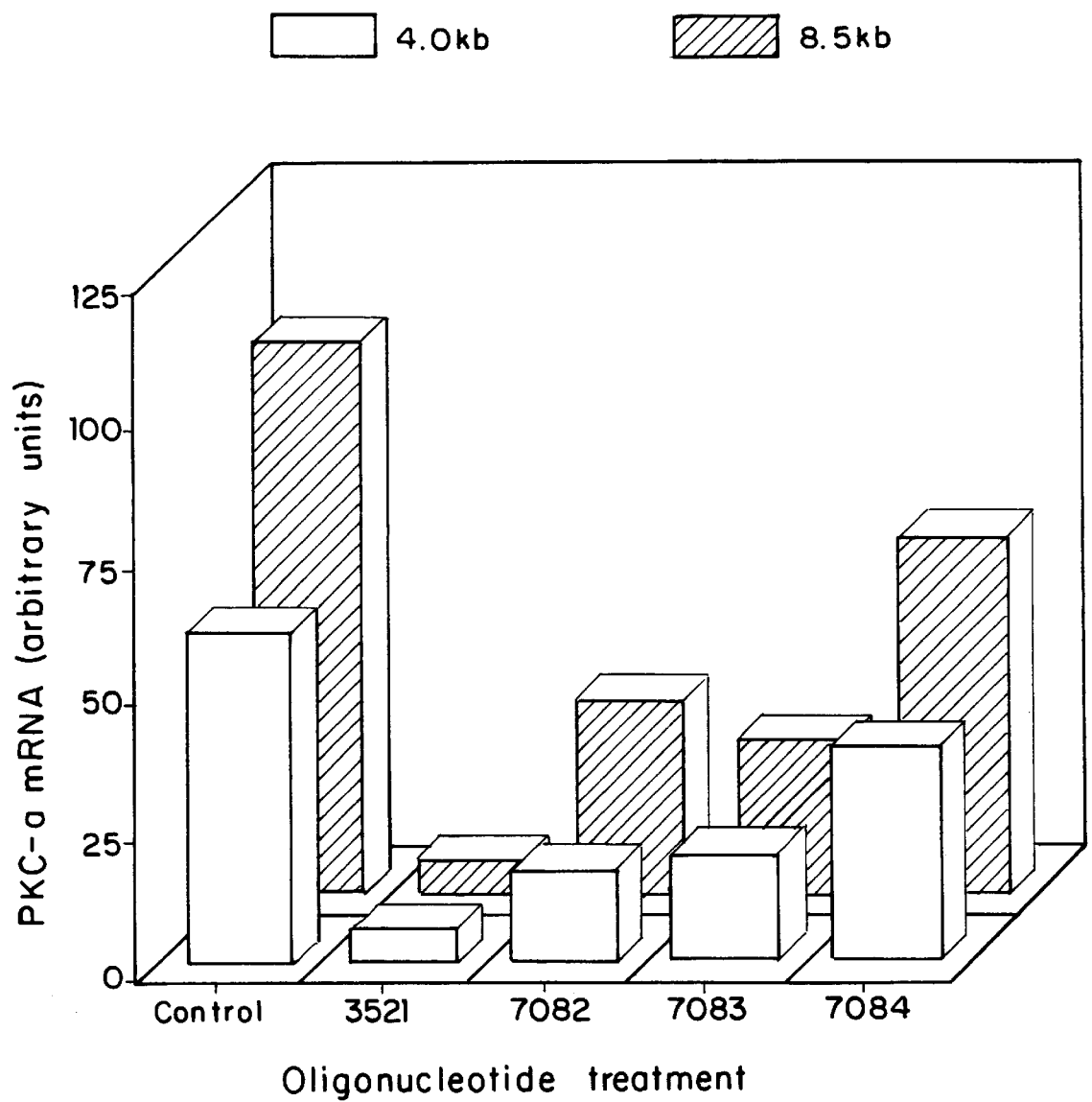

As shown in FIG. 9, oligonucleotides 6632, 6653, 7082 and 7083 are most active in reducing PKC-α mRNA levels.

Example 9

U-87 Human Glioblastoma Cell Culture and Subcutaneous Xenografts into Nude Mice

The U-87 human glioblastoma cell line was obtained from the ATCC Rockville, Md.) and maintained in Iscove's DMEM medium supplemented with heatted inactivated 10% fetal calf serum. Nude mice were injected subcutaneously with 2×10⁷ cells. Mice were injected intraperitoneally with ISIS 3521 at dosages of either 2 mg/kg or 20 mg/kg for 21 consecutive days beginning 7 days after xenografts were implanted. Tumor volumes were measured on days 14, 21, 24, 31 and 35. On day 35 (7 days after end of treatment), ISIS 3521 at 2 mg/kg had reduced tumor volume by 84% compared to saline or sense oligonucleotide control. The 20 mg/kg dose reduced tumor size by 91% on day 35.

Example 10

Effect of ISIS 3521 on PKC-α Protein Levels in U-87 Glioblastoma Xenografts in Nude Mice PKCα prot ein levels in subcutaneous U-87 tumor xenografts were measured by western blot analysis on day 24 (day 17 of treatment with ISIS 3521) and day 35 (7 days after end of treatment with ISIS 3521). An affinity-purifie d PKCα-specific polyclonal antibody (Life Technologies, Inc.) was used as the primary antibody. By day 24, ISIS 3521 was found to virtually totally abolish PKCα in the tumors. By seven days after cessation of oligonucleotide treatment (day 35), PKCα had returned to control levels.

Example 11

"Crossover Experiment" to Evaluate Effect of Switching Treatment on Tumor Size

Figure 10:
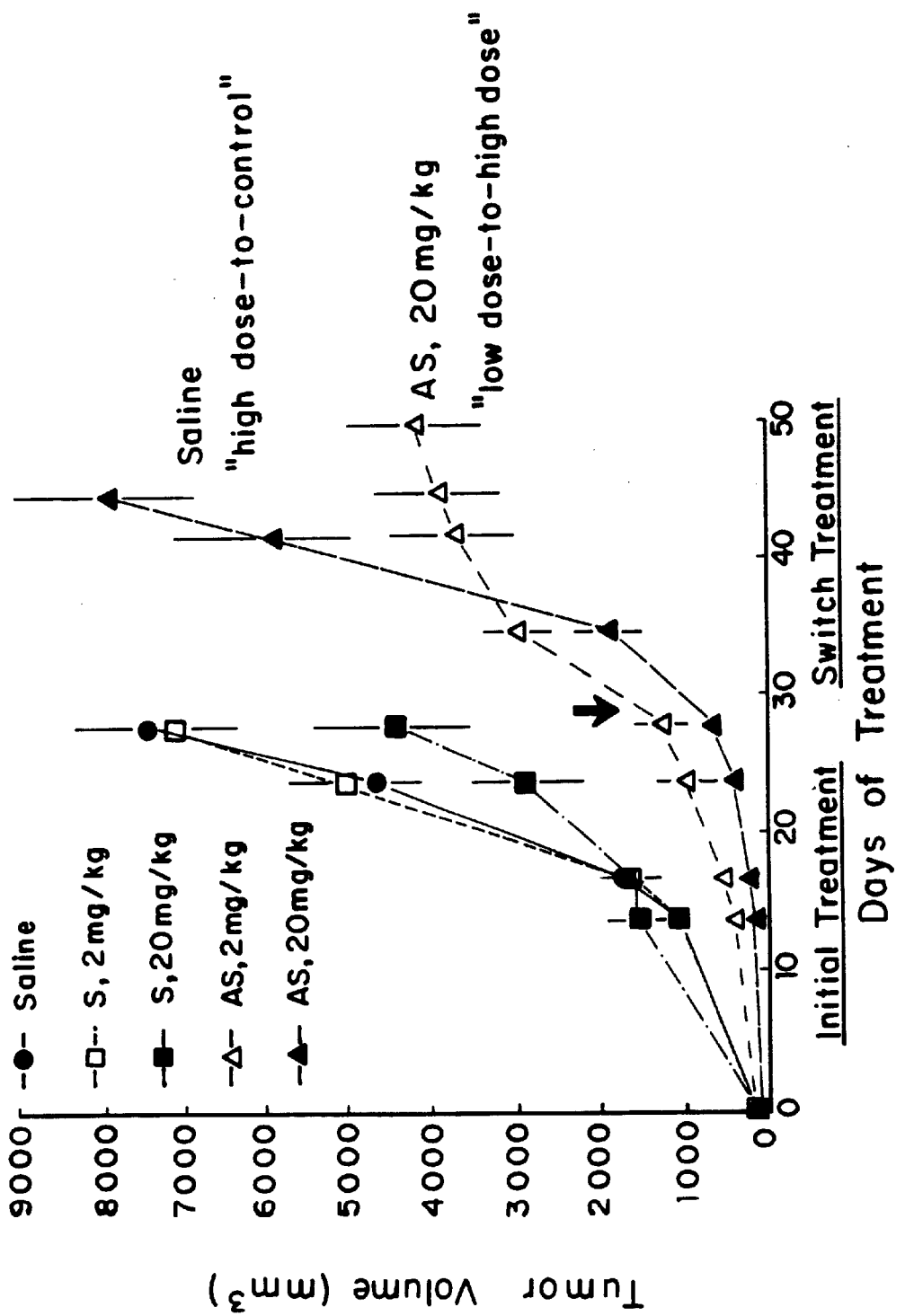
FIG. 10 is a line graph showing a "crossover" experiment to evaluate the effect of ISIS 3521 on U-87 glioblastoma cells in nude mice. The experiment was carried out with oligonucleotide doses of 2 mg/kg and 20 mg/kg and then treatment was switched (arrow). The group which had originally received ISIS 3521 at 20 mg/kg ("high dose-to-control" group, closed triangles) then received saline and the group which had originally received ISIS 3521 at 2 mg/kg ("low dose-to-high dose", open triangles) then received ISIS 3521 at 20 mg/kg. S=sense oligonucleotide (control); AS=antisense oligonucleotide (ISIS 3521) targeted to PKCA.

The two groups of mice with subcuta neous U-87 xenografts previously treated with ISIS 3521 (2 mg/kg or 20 mg/kg) were switched to different treatments on day 35 (7 days after the initial 21 day treatment had ended). The group which had previously received 20 mg/kg ISIS 3521 now received saline ("high dose-to-control"). The group which had received 2 mg/kg ISIS 3521 now received 20 mg/kg ISIS 3521 ("low dose-to-high dose"). This crossover treatment was continued for 21 days as for the original treatment. As shown in FIG. 10, the growth of the tumors in the "low dose-to-high dose" group (open triangles) leveled off after treatment was switched (arrow). The growth of the tumors in the "high dose-to-control" group (closed triangles) rapidly accelerated after switching to saline treatment (arrow). S=sense oligonucleotide (control); AS=antisense oligonucleotide (ISIS 3521) targeted to PKCα.

Example 12

Effect of ISIS 3521 on Intracerebral U-87 Glioblastoma Xenografts into Nude Mice U-87 cells were implanted in the brains of nude mice. Mice were treated via continuous intraperitoneal administration of antisense oligonucleotide ISIS 3521 (20 mg/kg), control sense oligonucleotide (20 mg/kg) or saline beginning on day 7 after xenograft implantation. All mice survived until day 25, at which point the saline-treated mice began to die. All saline-treated mice and sense oligonucleotide-treated mice were dead by day 41. In contrast, all ISIS 3521-treated mice were alive until approximately day 37, and half of the mice were still alive at day 61. At the termination of the experiment at day 80, 40% of the ISIS 3521-treated mice were still alive.

Example 13

Chimeric (deoxy gapped) 2'-O-methyl and 2'-methoxyethyl Oligonucleotides

Oligonucleotide 3521 (SEQ ID NO: 2) was chosen for further study and modification. Oligonucleotides having this sequence were synthesized as uniformly phosphorothioate chimeric oligonucleotides having a centered deoxy gap of various lengths flanked by 2'-O-methylated or 2'-O-methoxyethylated regions. Sequences are shown in Table 5. These oligonucleotides were tested for effects on PKC-α mRNA levels by Northern blot analysis as described in Example 6 with the following modifications. A549 cells were grown to 60–70% confluency, then washed twice with DME and then 5 ml of DME containing 20 μg/ml N-[1-(2,3-dioleyloxy)propyl]-n,n,n-trimethylammoniun chloride/dioleoylphosphatidyl-ethanolamine (DOTMA/DOPE also LIPOFECTIN®) with the indicated concentration of oligonucleotide. Results are shown in Table 6.

TABLE 5

Nucleotide Sequences of PKC-α Chimeric (deoxy gapped) 2'-O-methyl and 2'-O-methoxyethyl Oligonucleotides

| ISIS NO. | NUCLEOTIDE SEQUENCE (5'-> 3')[1] | SEQ ID NO: | TARGET GENE NUCLEOTIDE COORDINATES[2] | GENE TARGET REGION |
|---|---|---|---|---|
| 3521 | GsTsTsCsTsCsGsCsTsGsGsTsGsAsGsTsTsTsCsA | 2 | 2044–2063 | 3'-UTR |
| 11485 | GoToToCoToCoGoCoToGoGoToGoAoGoToToToCoA | 2 | 2044–2063 | 3'-UTR |
| 5357 | GsTsTsCsTsCsGsCsTsGsGsTsGsAsGsTsTsTsCsA | 2 | 2044–2063 | 3'-UTR |
| 8329 | GoToToCoToCoGsCsTsGsGsTsGsAsGoToToToCoA | 2 | 2044–2063 | 3'-UTR |
| 9606 | GsTsTsCsTsCsGsCsTsGsGsTsGsAsGsTsTsTsCsA | 2 | 2044–2063 | 3'-UTR |
| 9605 | GoToToCoToCoGsCsTsGsGsTsGsAsGoToToToCoA | 2 | 2044–2063 | 3'-UTR |
| 13009 | GsGsTsTsTsAsCsCsAsTsCsGsGsTsTsCsTsGsG | 23 | 9606 scrambled control | |

[1]Emboldened residues are 2'-methoxyethoxy residues, Underlined residues are 2'-methoxy (others are 2'-deoxy-). All 2'-methoxyethoxy cytidines are 5-methyl-cytidines; "s" linkages are phosphorothioate linkages, "o" linkages are phosphodiester linkages.
[2]Co-ordinates from Genbank Accession No. X52479.

TABLE 6

Dose Response of A549 Cells to PKC-α Antisense oligonucleotides (ASOs)

| ISIS # | SEQ ID No: | ASO Gene Target | Dose | % mRNA Expression | % mRNA Inhibition |
|---|---|---|---|---|---|
| control | — | — | — | 100% | — |
| 3521 | 2 | 3'-UTR | 25 nM | 91% | 9% |
| " | " | " | 50 nM | 74% | 26% |
| " | " | " | 100 nM | 42% | 58% |
| 5357 | 2 | 3'-UTR | 25 nM | 68% | 32% |
| " | " | " | 50 nM | 51% | 49% |
| " | " | " | 100 nM | 38% | 62% |
| 8329 | 2 | 3'-UTR | 25 nM | 111% | — |
| " | " | " | 50 nM | 108% | — |
| " | " | " | 100 nM | 105% | — |
| 9605 | 2 | 3'-UTR | 25 nM | 40% | 60% |
| " | " | " | 50 nM | 23% | 77% |
| " | " | " | 100 nM | 14% | 86% |
| 9606 | 2 | 3'-UTR | 25 nM | 44% | 56% |
| " | " | " | 50 nM | 23% | 77% |
| " | " | " | 100 nM | 14% | 86% |

ISIS 3521 (SEQ ID NO. 2) results in a concentration dependent reduction in PKC-α mRNA with an $IC_{50}$ of approximately 100 nM. ISIS 5357 (SEQ ID NO. 2) has an $IC_{50}$ of approximately 50 nM, while ISIS 8329 (SEQ ID NO. 2) shows no activity. The 2'-MOE oligonucleotides, ISIS 9605 (SEQ ID NO. 2) and ISIS 9606 (SEQ ID NO. $IC_{50}$'s of approximately 25 nM.

In additional experiments, the 2'-MOE oligonucleotides were able to reduce expression at 72 hours. The effect was sequence-specific and also specific to the PKC-α isozyme.

The effect of ISIS 9606 (SEQ ID NO. 2) on PKC-α protein levels was determined. A549 cells were treated with 100 nM oligonucleotide as described and protein expression was determined by Immunoblotting as described in Example 4. The PKC-α antibody was obtained from Upstate Biotechnology (Lake Placid, N.Y.). PKC-α protein expression was reduced in a time dependent manner and was consistent with the PKC-α half-life of approximately 24 hours.

The effect of ISIS 9606 (SEQ ID NO. 2) on PKC-α enzyme activity was determined. A549 cells were treated with oligonucleotides for three days. Cells were then washed in cold PBS, scraped and pelleted into a sample prepation buffer (50 nM Tris-HCl pH7.5, 5 mM EDTA, 10 nM EGTA, 50 nM 2-mercaptoethanol, 1 mM PMSF, 10 mM Benzamidine). A cytosolic fraction was prepared by centrifugation at 100,000× g for 1 hour at 4° C. PKC enzyme activity was determined by measuring the ability of the cytosolic protein extract to phosphorylate a synthetic peptide substrate in the absence or presence of phosphatidylserine in an ELISA based assay according to the manufacturer's instructions (MBL Co Ltd., Nagoya, Japan). The final concentrations of the reaction mixture used were 25 nM Tris-HCl, pH7.0, 3mM $MgCl_2$, 0.1 mM ATP, 2 mM $CaCl_2$, 0.5 mM EDTA, 1 mM EGTA, 5 mM 2-mercaptoethanol, +/− 50 μg/ml phosphatidylserine. PKC activity is defined as phosphatidylserine dependent kinase activity. Results are shown in Table 7.

TABLE 7

Effect of ISIS 9606 on PKC enzyme activity

| ISIS # | SEQ ID NO: | ASO Gene Target | Dose | % PKC Activity − Ps | % PKC Activity + Ps |
|---|---|---|---|---|---|
| basal | — | — | — | 4.3 | 2.90 |
| no oligo | — | — | — | 34.9 | 150.9 |
| 9606 | 2 | 3'-UTR | 100 nM | 14.9 | 38.6 |
| 13009 | 23 | control | 100 nM | 30.6 | 140.0 |

An overall reduction in PKC-α enzyme activity of approximately 70% was seen. Samples of protein extract used in the assay were analyzed by Western blotting to confirm a specific reduction of PKC-α protein expression by ISIS 9606 (SEQ ID NO. 2). The scrambled control, ISIS 13009 (SEQ ID NO. 23) had no effect on PKC-α protein expression or kinase activity.

Example 14

Effect of PKC-α Reduction on Phorbol Ester Mediated AP-1 Gene Expression in A549 Cells The effect of PKC-α reduction on AP-1 transcription factor components was determined. 12-O-tetradecanoylphorbol-13-acetate (TPA) causes a time dependent accumulation of mRNA transcripts of multiple members of AP-1, including c-jun, jun-B and c-fos.

A549 cells were treated with 100 nM ISIS 9606 (SEQ ID NO. 2) or ISIS 13009 (SEQ ID NO. 23) and DOTMA/DOPE as described in Example 13. Cells were then washed and allowed to recover for an additional 68 hours. Cells were then treated with 100 nM TPA for 30 minutes and the expression of either c-fos, jun-B, c-jun or G3PDH mRNA expression was determined by Northern blotting.

Total RNA was extracted from cells and resolved on agarose gels as described in Example 6. These were transferred to nylon membrane (Biorad, Hercules, Calif.) and probed with $^{32}P$ radiolabelled cDNA probes for different PKC isozymes. Additionally, gels were probed with $^{32}P$ radiolabelled cDNA probes for c-fos, c-jun, and junB (American Type Culture Collection, Manassas, Va.). Gels were routinely stripped and reprobed with radiolabelled human glycerol-3-phosphate dehydrogenase (G3PDH) probe to confirm equal loading. Radioactive bands were quantified using a Phospholmager (Molecular Dynamics, Sunnyvale, Calif.). Results are shown in Table 8. Upregulation of c-jun was almost completely inhibited. A scrambled control oligonucleotide was without effect on the up-regulation of any AP-1 family member. The induction of both c-fos and jun-B mRNA were unaffected by PKC-α depletion.

TABLE 8

Effect of ISIS 9606 on c-jun expression

| ISIS # | SEQ ID NO: | ASO Gene Target | Dose | % c-jun mRNA expression |
|---|---|---|---|---|
| basal | — | — | — | 100% |
| no oligo | — | — | — | 353% |
| 9606 | 2 | 3'-UTR | 100 nM | 173% |
| 13009 | 23 | control | 100 nM | 352% |

What is claimed is:

1. A method of treating an animal having a disease or condition associated with altered expression of c-jun comprising administering to said animal an antisense oligonucleotide specifically hybridizable with a nucleic acid encoding protein kinase C-α under conditions which decrease expression of c-jun, wherein said disease or condition is cancer of the bladder, bone, lung, ovary or central nervous system.

2. The method of claim 1 wherein said antisense oligonucleotide has at least one phosphorothioate internucleotide linkage, wherein said antisense oligonucleotide decreases expression of protein kinase C-α.

3. The method of claim 1 wherein said antisense oligonucleotide has at least one 2'-methoxyethoxy nucleotide, wherein said antisense oligonucleotide decreases expression of protein kinase C-α.

4. The method of claim 1 wherein said antisense oligonucleotide has a sequence comprising SEQ ID NO:2, wherein said antisense oligonucleotide decreases expression of protein kinase C-α.

* * * * *

UNITED STATES PATENT AND TRADEMARK OFFICE
CERTIFICATE OF CORRECTION

PATENT NO. : 6,300,320 B1
DATED : October 9, 2001
INVENTOR(S) : Dean et al.

It is certified that error appears in the above-identified patent and that said Letters Patent is hereby corrected as shown below:

Column 4,
Line 12, please delete "PKCA" and insert therefor -- PKCα --;

Column 5,
Line 60, please delete "intronl/exon" and insert therefor -- intron/exon --;

Column 6,
Line 3, please delete "fimction" and insert therefor -- function --;

Column 7,
Line 21, please delete "fimction" and insert therefor -- function --;

Column 8,
Line 5, please delete "firther" and insert therefor -- further --;
Line 28, please delete "intemucleoside" and insert therefor -- internucleoside --;

Column 9,
Line 11, please delete "intemucleoside" and insert therefor -- internucleoside --;

Column 13,
Line 48, please delete "phannaceutically" and insert therefor -- pharmaceutically --;

Column 18,
Line 64, please delete "a d ded" and insert therefor -- added --;
Line 64, please delete "additiona l" and insert therefor -- additional --;

Column 20,
Line 25, please delete "chromato-graphed" and insert therefor -- chromatographed --;
Line 26, please delete "EtOAcHexane" and insert therefor -- EtOAc/Hexane --;
Line 47, please delete "0.0054" and insert therefor -- 0.0054 --;

Column 21,
Line 1, please delete "fiume" and insert therefor -- fume --;
Line 48, please delete "(2-aformadoximinooxy)" and insert therefor
-- (2-formadoximinooxy) --;

Column 24,
Line 41, please delete "PKC-αa" and insert therefor -- PKC-α --;
Line 57, please delete "ol" and insert therefor -- phorbol --;

UNITED STATES PATENT AND TRADEMARK OFFICE
CERTIFICATE OF CORRECTION

PATENT NO. : 6,300,320 B1
DATED : October 9, 2001
INVENTOR(S) : Dean et al.

It is certified that error appears in the above-identified patent and that said Letters Patent is hereby corrected as shown below:

Column 27,
Line 43, please delete "PRNA" and insert therefor -- mRNA --;

Column 28,
Line 22, please delete "slated" and insert therefor -- unslated --;

Column 29,
Line 25, please delete "prot ein" and insert therefor -- protein --;
Line 29, please delete "purifie d" and insert therefor -- purified --;
Line 39, please delete "subcata neous" and insert therefor -- subcutaneous --.

Signed and Sealed this

Twenty-first Day of January, 2003

JAMES E. ROGAN
*Director of the United States Patent and Trademark Office*